(12) United States Patent
Tyber et al.

(10) Patent No.: US 10,864,081 B2
(45) Date of Patent: Dec. 15, 2020

(54) WEDGE OSTEOTOMY DEVICE AND METHOD OF USE

(71) Applicant: Tyber Medical LLC, Morristown, NJ (US)

(72) Inventors: Jeffrey Tyber, Landing, NJ (US); Christopher Faresich, Denville, NJ (US)

(73) Assignee: Tyber Medical, LLC, Bethlehem, PA (US)

( * ) Notice: Subject to any disclaimer, the term of this patent is extended or adjusted under 35 U.S.C. 154(b) by 496 days.

(21) Appl. No.: 14/513,300

(22) Filed: Oct. 14, 2014

(65) Prior Publication Data
US 2015/0032220 A1    Jan. 29, 2015

Related U.S. Application Data

(63) Continuation-in-part of application No. 14/054,100, filed on Oct. 15, 2013, now Pat. No. 9,387,087.
(Continued)

(51) Int. Cl.
*A61F 2/02* (2006.01)
*A61F 2/28* (2006.01)
(Continued)

(52) U.S. Cl.
CPC ............ *A61F 2/28* (2013.01); *A61B 17/7059* (2013.01); *A61B 17/80* (2013.01);
(Continued)

(58) Field of Classification Search
CPC . A61B 17/7059; A61B 17/80; A61B 17/8052; A61B 17/8095; A61B 17/86; A61F 2/44; A61F 2/442
(Continued)

(56) References Cited

U.S. PATENT DOCUMENTS 4,759,351 A * 7/1988 Slocum .............. A61B 17/1668
606/103
5,152,791 A   10/1992 Hakamatsuka et al.
(Continued)

FOREIGN PATENT DOCUMENTS

WO    WO2007098288    8/2007

OTHER PUBLICATIONS

PCT/US2014/060338 International Preliminary Report on Patentability. dated Apr. 28, 2016. 11 pages.
(Continued)

*Primary Examiner* — Jessica Weiss
(74) *Attorney, Agent, or Firm* — Joseph E. Maenner; Maenner & Associates, LLC

(57) ABSTRACT

An orthopedic implant system includes a wedge implant. The implant includes a body having an upper surface extending generally in a first plane. The upper surface has a first plurality of longitudinal grooves and a second plurality of transverse grooves extending therealong. Portions of the upper surface extend between adjacent longitudinal grooves and transverse grooves form individual peaks. A lower surface extends generally in a second plane, parallel to the first plane. The lower surface has a third plurality of longitudinal grooves and a fourth plurality of transverse grooves extending therealong. Portions of the lower surface extend between adjacent longitudinal grooves and transverse grooves form individual peaks.

23 Claims, 21 Drawing Sheets

Related U.S. Application Data

(60) Provisional application No. 61/715,891, filed on Oct. 19, 2012.

(51) Int. Cl.

| | | |
|---|---|---|
| *A61F 2/46* | (2006.01) | |
| *A61B 17/86* | (2006.01) | |
| *A61B 17/80* | (2006.01) | |
| *A61B 17/70* | (2006.01) | |
| *A61F 2/44* | (2006.01) | |
| *A61B 90/94* | (2016.01) | |
| *A61F 2/30* | (2006.01) | |
| *A61B 90/00* | (2016.01) | |

(52) U.S. Cl.
CPC ...... *A61B 17/8052* (2013.01); *A61B 17/8095* (2013.01); *A61B 17/86* (2013.01); *A61B 17/863* (2013.01); *A61B 17/865* (2013.01); *A61B 90/94* (2016.02); *A61F 2/4455* (2013.01); *A61F 2/4465* (2013.01); *A61F 2/4603* (2013.01); *A61F 2/4611* (2013.01); *A61B 17/8645* (2013.01); *A61B 2090/037* (2016.02); *A61F 2/30771* (2013.01); *A61F 2002/2817* (2013.01); *A61F 2002/3008* (2013.01); *A61F 2002/30011* (2013.01); *A61F 2002/3071* (2013.01); *A61F 2002/3082* (2013.01); *A61F 2002/3092* (2013.01); *A61F 2002/3093* (2013.01); *A61F 2002/30281* (2013.01); *A61F 2002/30355* (2013.01); *A61F 2002/30507* (2013.01); *A61F 2002/30578* (2013.01); *A61F 2002/30593* (2013.01); *A61F 2002/30774* (2013.01); *A61F 2002/30808* (2013.01); *A61F 2002/30836* (2013.01); *A61F 2002/30843* (2013.01); *A61F 2002/4627* (2013.01); *A61F 2310/00407* (2013.01); *A61F 2310/00461* (2013.01); *A61F 2310/00796* (2013.01)

(58) Field of Classification Search
USPC .......... 623/17.11–17.16; 606/86 R, 87, 279
See application file for complete search history.

(56) References Cited

U.S. PATENT DOCUMENTS

| | | | |
|---|---|---|---|
| 5,766,251 A * | 6/1998 | Koshino | A61F 2/28 606/246 |
| 5,888,227 A | 3/1999 | Cottle | |
| 6,008,433 A * | 12/1999 | Stone | A61B 17/68 623/20.14 |
| 6,096,080 A * | 8/2000 | Nicholson | A61B 17/1757 623/17.16 |
| 6,261,291 B1 | 7/2001 | Talaber et al. | |
| 6,306,170 B2 | 10/2001 | Ray | |
| 6,432,106 B1 * | 8/2002 | Fraser | A61F 2/30771 606/283 |
| 6,790,233 B2 | 9/2004 | Brodke et al. | |
| 7,238,203 B2 | 7/2007 | Bagga et al. | |
| 7,641,690 B2 | 1/2010 | Abdou | |
| 8,216,312 B2 * | 7/2012 | Gray | A61B 17/7059 606/249 |
| 8,506,636 B2 | 8/2013 | Dye | |
| 8,556,972 B2 | 10/2013 | Gordon et al. | |
| 9,358,127 B2 * | 6/2016 | Duffield | A61F 2/4455 |
| 9,788,967 B2 | 10/2017 | Jo | |
| 2001/0049560 A1 * | 12/2001 | Paul | A61F 2/28 623/17.16 |
| 2003/0125739 A1 * | 7/2003 | Bagga | A61F 2/4455 606/247 |
| 2004/0082998 A1 * | 4/2004 | Shinomiya | A61L 27/46 623/17.11 |
| 2004/0243241 A1 | 12/2004 | Iatephanous et al. | |
| 2005/0010215 A1 | 1/2005 | Delecrin et al. | |
| 2005/0075641 A1 * | 4/2005 | Singhatat | A61B 17/15 606/86 R |
| 2005/0101960 A1 | 5/2005 | Fiere et al. | |
| 2006/0036322 A1 * | 2/2006 | Reiley | A61B 17/1615 623/17.11 |
| 2006/0116766 A1 | 6/2006 | Lemaire | |
| 2007/0270844 A1 | 11/2007 | Lin et al. | |
| 2008/0021557 A1 * | 1/2008 | Trieu | A61L 27/26 623/17.15 |
| 2008/0230421 A1 | 9/2008 | Pleil et al. | |
| 2008/0243135 A1 | 10/2008 | Robinson | |
| 2008/0300634 A1 * | 12/2008 | Gray | A61B 17/7059 606/280 |
| 2009/0036926 A1 | 2/2009 | Hestad et al. | |
| 2009/0048675 A1 * | 2/2009 | Bhatnagar | A61B 17/0642 623/17.16 |
| 2009/0182430 A1 | 7/2009 | Tyber et al. | |
| 2010/0152853 A1 | 6/2010 | Kirschman | |
| 2010/0290091 A1 | 11/2010 | Kirschman | |
| 2011/0082551 A1 * | 4/2011 | Kraus | A61F 2/30771 623/17.11 |
| 2011/0106171 A1 | 5/2011 | Kirschman | |
| 2011/0172780 A1 * | 7/2011 | Scheland | A61B 17/8061 623/18.11 |
| 2011/0184478 A1 * | 7/2011 | Reiley | A61B 17/1615 606/86 R |
| 2011/0224734 A1 | 9/2011 | Schelling | |
| 2012/0130496 A1 * | 5/2012 | Duffield | A61B 17/7059 623/17.16 |
| 2013/0211522 A1 * | 8/2013 | Weiss | A61F 2/2846 623/16.11 |
| 2013/0238095 A1 | 9/2013 | Pavento et al. | |
| 2013/0268080 A1 | 10/2013 | Melkent et al. | |
| 2014/0031935 A1 | 1/2014 | Donner et al. | |
| 2014/0128980 A1 * | 5/2014 | Kirschman | A61F 2/447 623/17.16 |
| 2015/0018956 A1 * | 1/2015 | Steinmann | A61F 2/447 623/17.16 |
| 2015/0088256 A1 * | 3/2015 | Ballard | A61B 17/708 623/17.11 |
| 2015/0305752 A1 * | 10/2015 | Eash | A61B 17/157 606/82 |
| 2016/0151167 A1 | 6/2016 | Jo | |
| 2016/0310286 A1 | 10/2016 | McJunkin | |

OTHER PUBLICATIONS

Office Action for U.S. Appl. No. 14/054,100, dated Oct. 23, 2015.
International Search Report and Written Opinion for PCT/US2014/060338, dated Jan. 19, 2015. 16 pages.
www.footandanklefixation.com/product/wright-medical-biofoam/. Printed Oct. 20, 2014. 9 pages.
www.arthrex.com/osferion-osteotomy-wedge. Printed Oct. 30, 2014. 3 pages.
PCT/US2017/042496, International Search Report and Written Opinion, dated Dec. 17, 2017. 12 pages.

\* cited by examiner

WEDGE OSTEOTOMY DEVICE AND METHOD OF USE

CROSS-REFERENCE TO RELATED APPLICATIONS

The present application is a Continuation-in-Part application of U.S. patent application Ser. No. 14/054,100, filed on Oct. 15, 2013, which claims priority from U.S. Provisional Patent Application Ser. No. 61/715,891, filed on Oct. 19, 2012, both of which are incorporated by reference herein in their entireties.

FIELD OF THE INVENTION

The present invention generally relates to a wedge implant that is inserted into an osteotomy incision to stabilize and reposition a portion of bone.

BACKGROUND OF THE INVENTION

An osteotomy is a surgical procedure that involves cutting and removing a portion of bone, such as, for example, the calcaneus. Wedge osteotomies utilize a wedge implant to reposition and stabilize the bone on either side of the cut.

Typically, osteotomy wedge implants are constructed from inert biocompatible material such as titanium or polyether-ether-ketone (PEEK). Titanium is typically used in orthopedic systems due to its strength and osteoconductive properties. However, in intervertebral spacers, titanium is not the preferred choice due to its high stiffness compared with bone. The large stiffness differential between bone and titanium has caused a high incidence of subsidence of the implant into the vertebral body. This has led the way for other biomaterials being selected for the spacer's body material. PEEK is a common interbody material selected because the Young's Modulus is extremely similar to bone and the material is extremely inert. However, PEEK is not an osteoconductive material and a large central oval cavity is the only space designed for bone through growth, thus the spacers remove a larger percentage of the fusion area.

Prior art wedge implant, such as, for example, the Arthrex product line, feature a metatarsal opening wedge plate system in which the plate is secured over the osteotomy and a bone wedge is implanted into the osteotomy space. One perceived problem with this open wedge osteotomy system is the loss of bone correction due to mechanical failure of the bone implant.

The Wright Medical BIOFOAM Wedge System provides a porous titanium wedge implant. The procedure using this system involves opening in osteotomy, implanting the wedge into the bone space, and then securing a plate over the osteotomy site. One perceived problem with this system is the radiolucency of the porous titanium implants. The titanium implant shows up during MRI, CT, and x-ray scans, making postoperative imaging impossible.

The Arthrex OSferion System provides a synthetic, porous β-TCP bone wedge for femoral and tibial wedge osteotomies. The OSferion bone wedge is constructed from an osteoconductive bone graft substitute and a β-TCP bone void filler.

It would be beneficial to provide an osteotomy wedge implant that is radio transparent, to enable a clinician to view phone on either side of the wedge implant, and osteoconductive, to maximize the bone fusion area.

BRIEF SUMMARY OF INVENTION

In accordance with one exemplary embodiment of invention, an osteotomy implant includes a first surface extending generally in a first plane. The first surface has a first plurality of longitudinal grooves and a second plurality of transverse grooves extending therealong. Portions of the first surface extend between adjacent longitudinal grooves and transverse grooves form individual peaks. A second surface extends generally in a second plane, oblique to the first plane. The second surface has a third plurality of longitudinal grooves and a fourth plurality of transverse grooves extending therealong. Portions of the second surface extend between adjacent longitudinal grooves and transverse grooves form individual peaks. Each of the first surface and the second surface includes an osteoconductive coating, such as a titanium plasma spray coating.

In accordance with another exemplary embodiment of the present invention, an osteotomy implant system comprises a generally, wedge shaped core constructed from a radio translucent material. The body has a central plane extending through the body. A first generally planar bone engaging surface extends at an acute angle relative to the central plane on a first side of the core. A second generally planar bone engaging surface is disposed on an opposing side of the central plane from the first generally planar bone engaging surface on a second side of the core. The second generally planar bone engaging surface extends at the acute angle relative to the central plane. Each of the first and second generally planar bone engaging surfaces includes an osteoconductive coating, such as a titanium plasma spray coating. Each of the first and second generally planar bone engaging surfaces has a surface roughness of greater than about 0.006 Ra in microns.

Additionally, the present invention provides a method of inserting a wedge to stabilize and reposition a bone. The method comprises the steps of making a cut in bone at an osteotomy site; inserting a wedge tool into the cut; and inserting a wedge into the cut, the wedge having an osteoconductive coating.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 43 is a perspective view of the osteotomy implant shown in FIGS. 39-42 inserted into a bone of a foot.

DETAILED DESCRIPTION OF EXEMPLARY EMBODIMENTS

Figure 1:
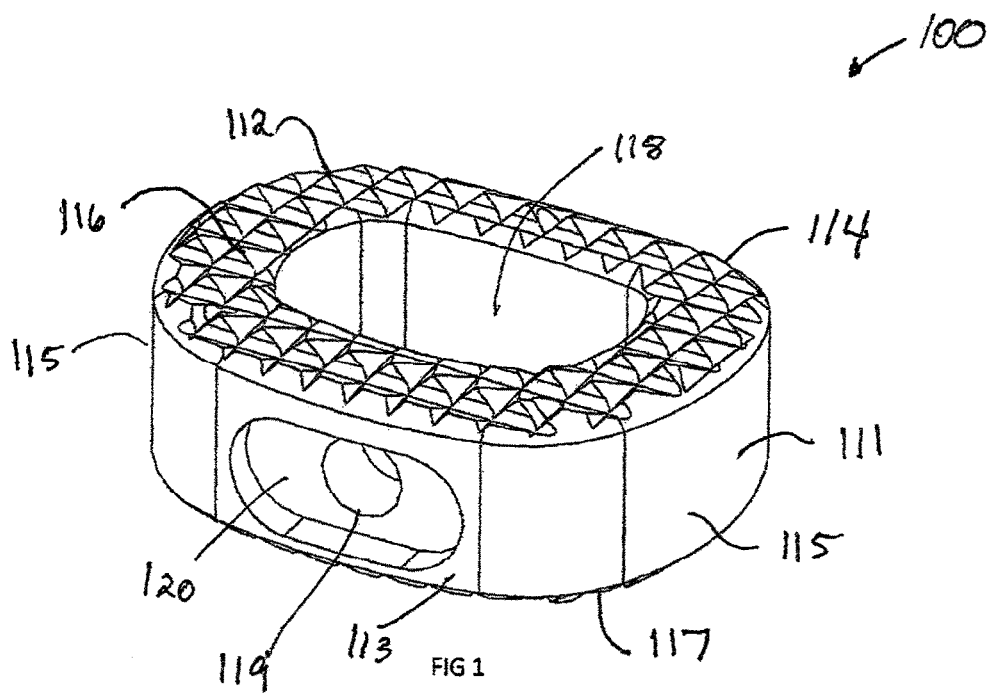
FIG. 1 is a perspective view of an intervertebral implant in accordance with one exemplary embodiment of the invention.

In the drawings, like numerals indicate like elements throughout. Certain terminology is used herein for convenience only and is not to be taken as a limitation on the present invention. For purposes of this description, the terms "anterior", "posterior", "superior" and "inferior" describe the position of surfaces or features relative to the anatomy. The term "anterior" refers to features having a relative position toward the front side of a spine, and "posterior" refers to features having a relative position toward the rear side of the spine. The term "superior" refers to features having a relative position above other features, in the cranial direction, and the term "inferior" refers to features having a relative position below other features in a caudal direction. The terminology includes the words specifically mentioned, derivatives thereof and words of similar import.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Applicant has observed a number of problems with the existing intervertebral spacers which use unsuitable materials, such as titanium or Polyether-ether ketone (PEEK). Interbody cages constructed from rigid materials such as titanium tend to have a large Young's modulus in the range of 105-130 GPa compared to bone, which has a relatively low modulus of 1.8 GPa. This makes titanium at least 58 times stiffer than bone and clinical studies have concluded this as the main cause of subsidence within the vertebral endplates. Subsidence is where the implant breaks through the vertebral endplates and intervertebral spacing is lost. Subsidence has been linked to pseudo-arthrosis, non-unions and re-operations of the fusion site. The high material stiffness may also enhance stress shielding of the central graft preventing or delaying bone through growth. However, the surface of titanium is well known for its osteoconductive properties. Osteoconductive materials encourage cell adhesion to the surface and can act like bone itself. This property can be used to increase the fusion area and allow bone growth directly on the implant.

The other well utilized material for intervertebral spacers is PEEK. PEEK is a semicrystalline thermoplastic with excellent mechanical and chemical resistance properties that are retained to high temperatures. In intervertebral fusion, intervertebral spacers constructed from PEEK have found a growing usage due to their relatively low stiffness, approximately 3.6 GPa compared to 1.8 GPa for bone. Clinical literature has reported lower occurrences of subsidence with PEEK intervertebral spacers, compared to a titanium spacer. However, PEEK is not an osteoconductive material and as such placement of a PEEK spacer within the intervertebral disc space can reduce the fusion area 60-70%, thus lowering the chances of a full fusion.

The intervertebral spacers of the present invention improve upon prior approaches by addressing the subsidence and settling of the endplates, while maximizing the fusion area. The various embodiments of the present invention allow proper load distribution through the use of low stiffness material enabling the load to transfer through the bone graft material during implant settling, while increasing the fusion area and reducing the mitigation risks. To accomplish this, the embodiments include an osteoconductive material, such as titanium, applied on a substrate with similar properties to bone. The inferior and superior surfaces are configured to maximize the surface area through the use of a rectangular pyramid shaped tooth. The assembly also includes a mechanism which can engage both an insertion instrument and supplemental hardware, such as a plate and screw assembly.

Referring now to FIG. 1, an interbody spacer 100 in accordance with one exemplary embodiment of the invention is shown. Interbody assemblies in accordance with the present invention may include a variety of body and teeth configurations. Interbody spacer 100 includes a rigid body 111 and a plurality of peaks, or teeth, 112 which form rigid body 111.

Rigid body 111 has an anterior surface 113 and a posterior surface 114 that is generally parallel to the anterior surface. Anterior surface 113 has a larger external surface area than posterior surface 114. Anterior and posterior surfaces 113, 114, respectively, are joined by a pair of lateral side surfaces 115 that extend generally radially to one another. A superior end surface 116 extends generally in a first plane and an inferior end surface 117 extends generally in a second plane obliquely, in a non-parallel manner, to the first plane between anterior side surface 113 and posterior side surface 114. Superior and inferior end surfaces 116, 117, respectively, taper or converge toward one another as end surfaces 116, 117 extend toward posterior side surface 114, forming a wedge-shaped structure. The anterior, posterior and lateral side surfaces, 113, 114, and 115, respectively, surround a generally centrally located cavity 118 that forms a space for fusion material, such as a bone graft or bone graft substitute.

Figure 10:
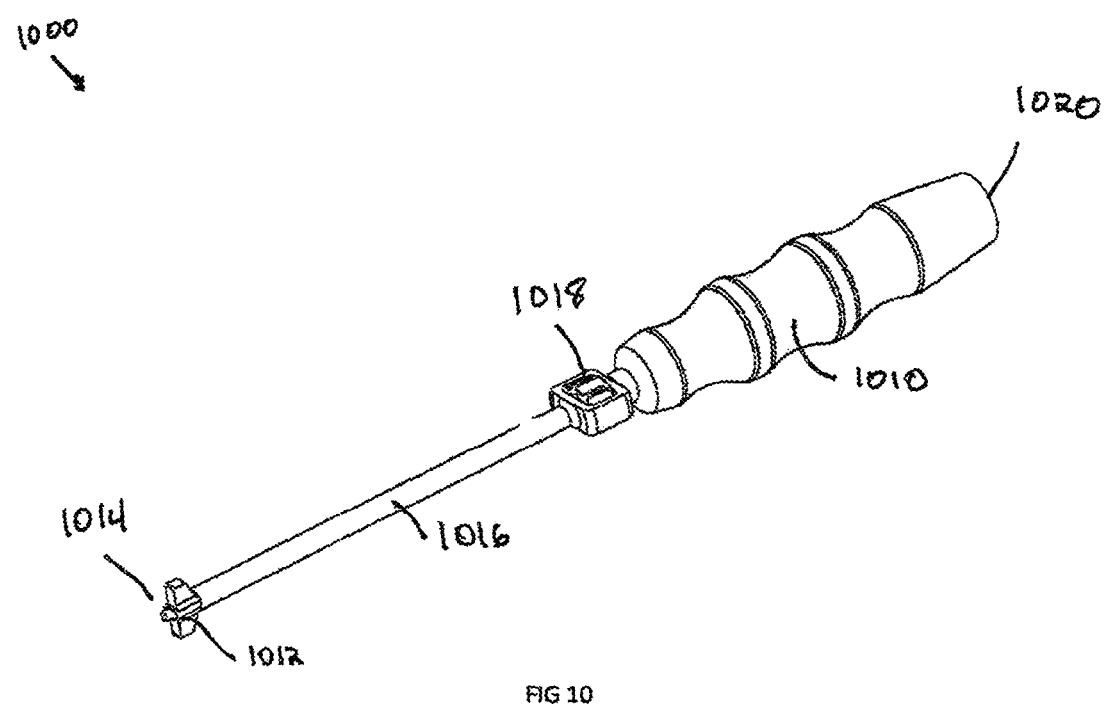
FIG. 10 is a perspective view of an alternative exemplary embodiment view of an insertion instrument.
Figure 15:
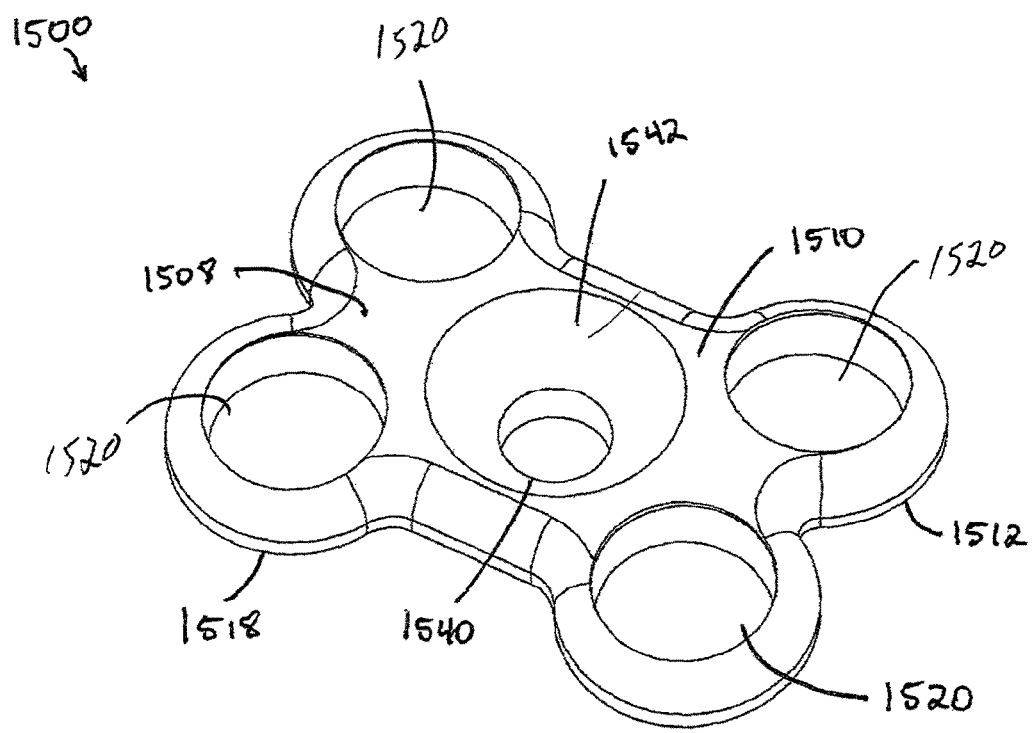
FIG. 15 is a perspective view of a plate for attachment to an intervertebral implant of FIG. 1, in accordance with one exemplary embodiment of the invention.

Interbody spacer 100 includes a recess 120 extending through anterior surface 113 inwardly toward cavity 118 and generally centered between the superior 116 and inferior 117 surfaces. Recess 120 allows for the alignment of a congruent extension 1012 from either an instrument such as an insertion instrument 1000, shown in FIG. 10, or an implant assembly such as plate assembly 1500, shown in FIG. 15. An aperture 119 is centrally located within the recess 120 between the anterior surface 113 and the cavity 118. The aperture 119 may be configured in either a threaded configuration, interference configuration or any means to secure the interbody spacer 100 to a separate device.

Figure 2:
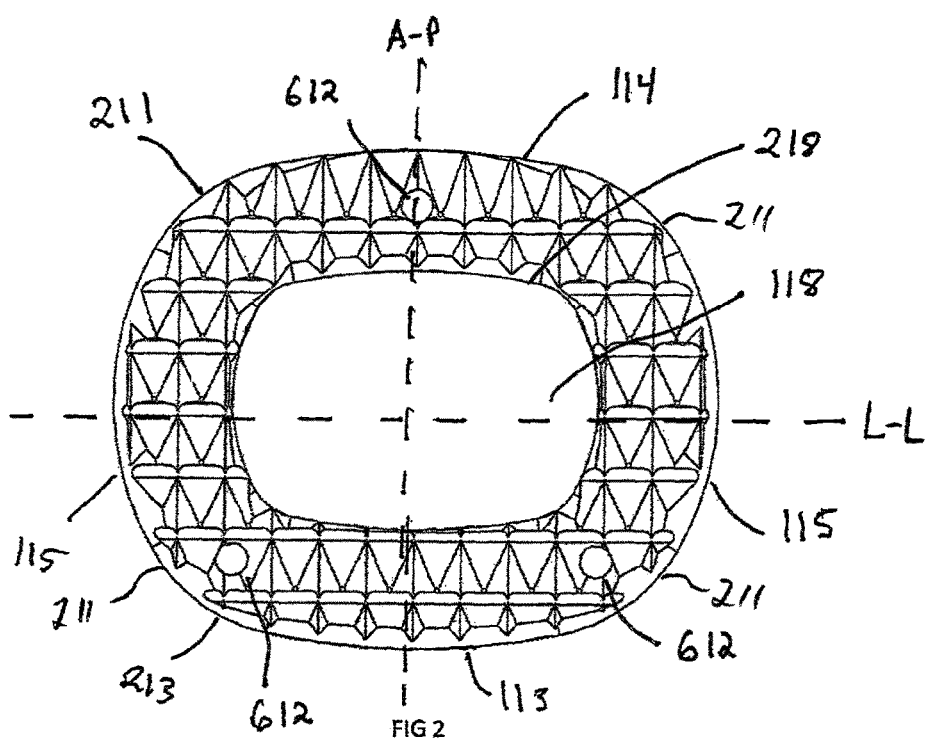
FIG. 2 is a top view of the implant of FIG. 1.

FIG. 2 illustrates a top view of the interbody spacer 100 having a generally oval shape. This shape is generated by rounding the anterior 113, posterior 114, and lateral surfaces 115, as well as the corner surfaces 211. The central opening 118 can be constructed by creating a uniform offset of the outer perimeter 213. The interbody spacer 100 benefits from a uniform geometry allowing the interbody to more evenly distribute the load distribution on the vertebral endplates. The center line A-P is defined by a line passing from the anterior surface 113 to the posterior surface 114. The L-L line is defined by a line passing from the lateral surface 115 to the other lateral surface 115. The teeth 112 are formed by adjacent ones of a plurality of anterior grooves 311 (shown in FIG. 3) traversing longitudinally along the A-P direction and a plurality of lateral grooves 411 (shown in FIG. 4) traversing transversely along the L-L direction. The intersection of anterior groove 311 and lateral groove 411 create a four sided pyramid-like tooth that maximize the surface area of superior surface 116 and inferior surface 117. While a four sided tooth is shown, those skilled in the art will recognize that tooth (not shown) can have more or less than four sides. The teeth 112 are used to grip the superior and inferior endplate of the vertebral body (not shown).

Figure 3:
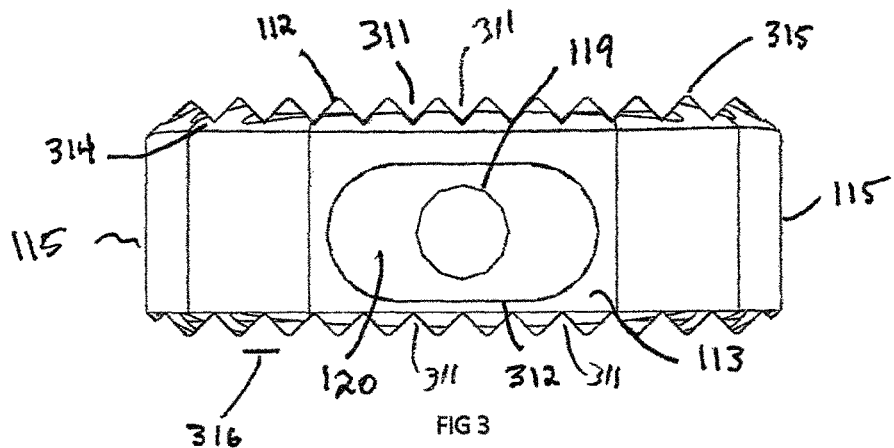
FIG. 3 is a front view of the implant of FIG. 1.

FIG. 3 illustrates the interbody spacer 100 from the anterior direction and shows the recess 120 and aperture 119. The recess 120 is defined by parallel edge 312, which forms a line segment and can be used to block rotation of congruent extension 1012 during insertion of the interbody spacer 100 into a patient (not shown). The teeth 112 are defined by the "V" shaped anterior groove 311, however this groove can be a "U" shaped groove, "L" shape groove, "O" shape groove or any other configuration of groove which is create by a low peak (or trough) 314, a high peak 315, and peak width 316.

Figure 4:
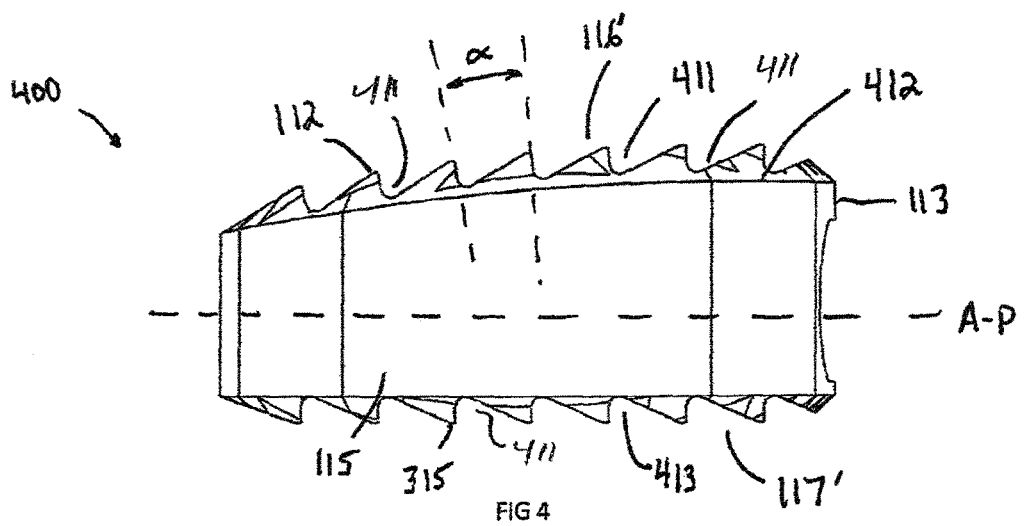
FIG. 4 is a side view of the implant of FIG. 1.

FIG. 4 illustrated a side profile of an interbody spacer 100, which is shown as having a non-symmetric shape 400. The implant superior surface 116' and inferior surface 117' cannot be mirrored about the A-P axis, thus defining the non-symmetric shape. The superior surface 117' is defined by a superior convex dome 412 in an anterior-posterior direction, which is used to match the inferior vertebral endplate, not shown. The teeth 112 viewed from a lateral direction are constructed from an "L" shape groove 413 in the L-L direction. In order to maintain equal distance between peaks 315 on a domed surface, the teeth 112 must repeat at a crest angle (α), where crest angle α is greater than 0 degrees. Exemplary values for crest angle α may be between about 0 degrees and about 90 degrees. In an exemplary embodiment, crest angle α is about 10 degrees. The surfaces of adjacent peaks that define angle α extend generally perpendicular to the domed surface. The inferior surface 117' teeth 112 are parallel to the A-P line and crest angle α is approximately 0 degrees between high peaks 315.

Figure 5:
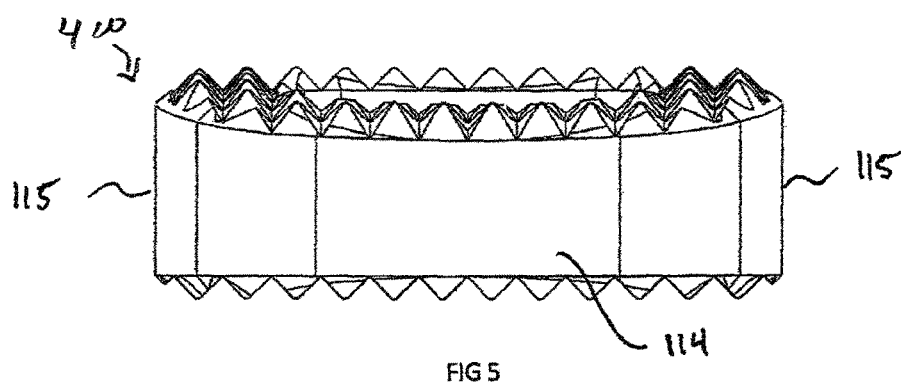
FIG. 5 is a rear view of the implant of FIG. 1.

FIG. 5 shows a posterior view of the interbody spacer 400, which shows the overall wedge shaped. In an exemplary embodiment, the posterior surface 114 is a wedge shape to aid in the insertion of the interbody spacer 100 into the vertebral disc space.

Figure 6:
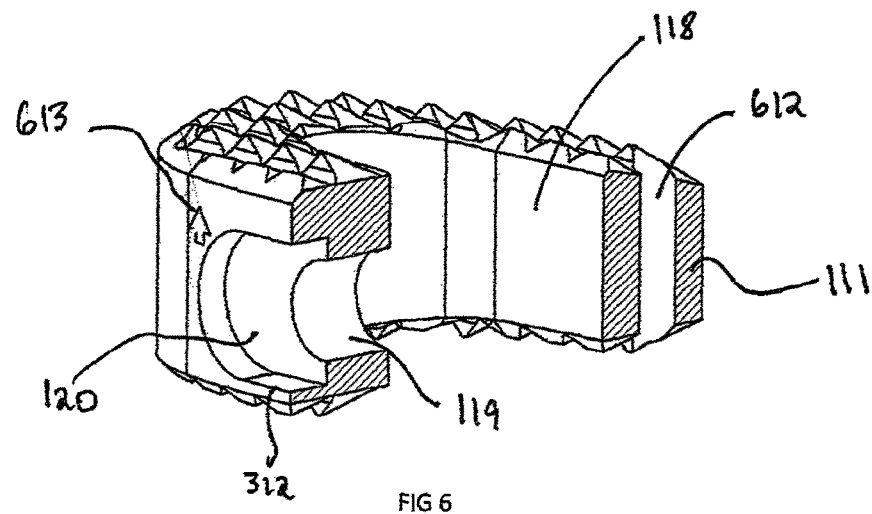
FIG. 6 is a cross section view of the intervertebral implant of FIG. 1, showing a hole configuration.

FIG. 6 shows the cross-sectional view of the interbody spacer 100 as well as the recess 120, aperture 119 and a marker bore 612. The recess 120 extends sufficiently into the interbody rigid body 111 enough to create a parallel edge 312. The aperture 119 extends from the recess 312 into the central opening 118. Marker bore 612 generally is a cylindrical in shape, however this can be rectangular, triangular, or other suitable shape. Marker bore 612 is used to insert marker 1251 (shown in FIG. 12b), which can be constructed from any radiopaque material, such as stainless steel, titanium, tantalum, etc. Generally there are a total of three marker bores 612 and corresponding markers 1251 spaced along the perimeter of interbody spacer 100. The markers 1251, when viewed from an anterior direction, show the interbody spacer's 100 width, which is defined from lateral surface 115 to opposing surface lateral surface 115. The markers 1251 when viewed from the lateral position show the depth of the implant. The depth is defined as the distance between the anterior surface 113 and the posterior surface 114.

Figure 7:
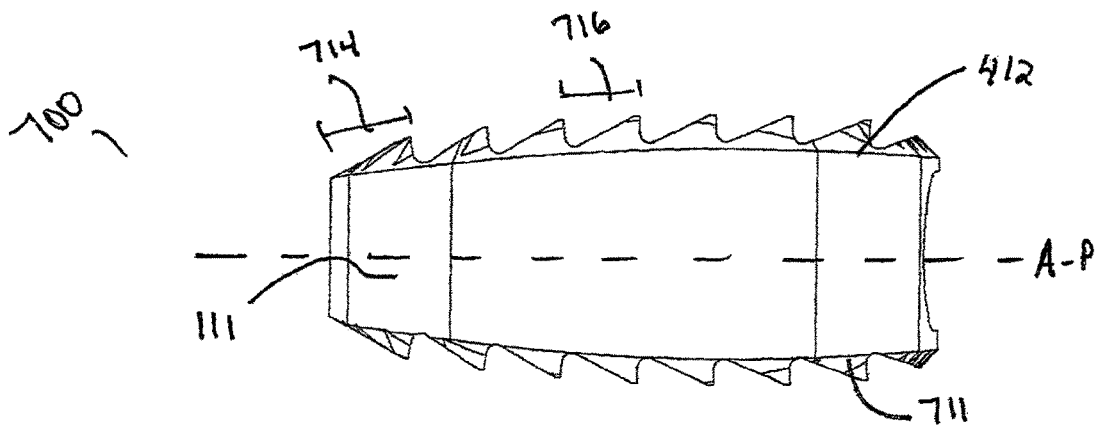
FIG. 7 is a side view of the implant of FIG. 1 with a first alternative exemplary type of surface.
Figure 8:
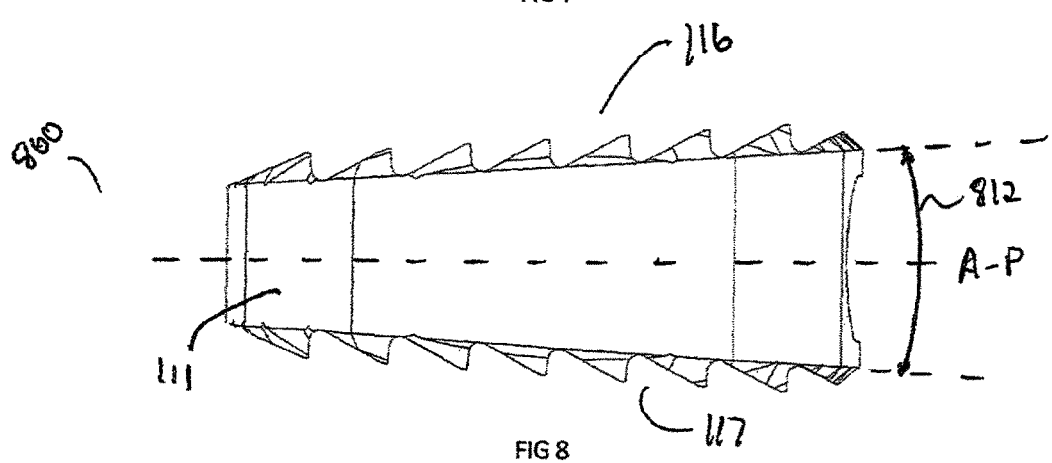
FIG. 8 is a side view of the implant of FIG. 1 with a second alternative exemplary type of surface.

FIGS. 7 and 8 show side views of an alternative embodiment of curved symmetric interbody spacer 700 and straight symmetric interbody spacer 800, respectively, where the superior surface 116 and inferior surface 117 are symmetric about the A-P line. In certain regions of the spine, such as lumbar or thoracic regions symmetrical interbody spacers 700 and 800 may mate with the opposing vertebral endplates better than a non-symmetric interbody spacer 400. The symmetric interbodies 700 and 800 are defined when the superior dome 412 or superior surface 116 can be mirrored about the A-P centerline to be equivalent to the inferior dome 711 or inferior surface 117. Another feature that can aid the insertion of the symmetric interbody spacer 700 and 800 in between the vertebral endplates is the width of rear crest 714. The width of rear crest 714 is generally larger than the width of mid crest 716, which allows for the interbody spacers 400, 700 and 800 to wedge itself between the vertebral endplates. The rear crest 714 can be aided by aligning the superior 116 and inferior 117 surfaces at an angle 812 from the A-P centerline. In an exemplary embodiment, angle 812 can be between about 0 degrees and about 90 degrees. In addition, the angle 812 can be used to match the spine curvature, such as Kyphosis or Lordosis angles.

Figure 9:
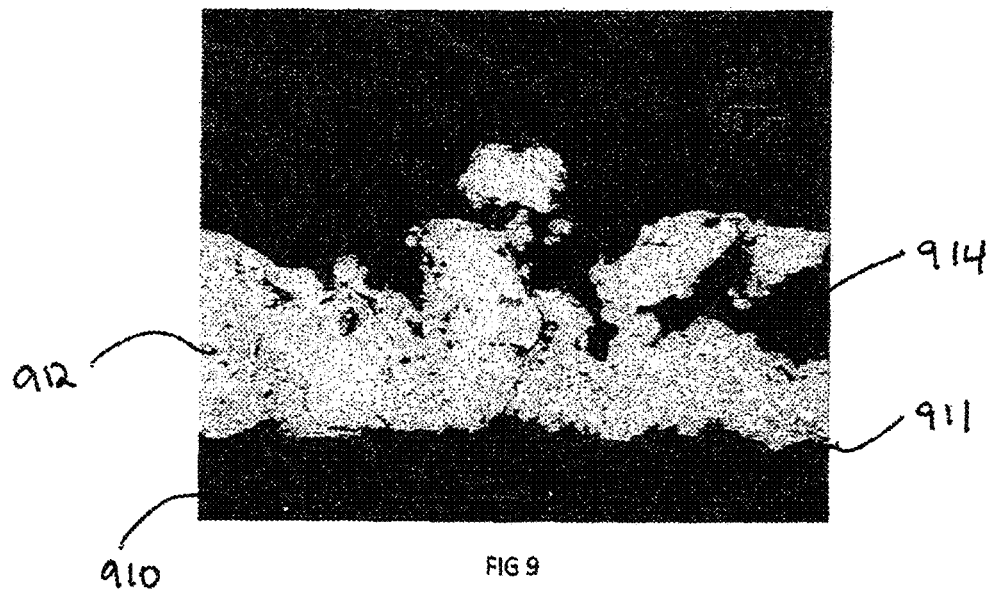
FIG. 9 is a micrograph showing distribution of titanium on a PEEK substrate, providing an illustrative exemplary composition of the invention.

FIG. 9 is a micrograph of a cross sectional cut of a substrate 910 and porous coating 912 on the surface of an interbody spacer 100, including at least one side of each of the the teeth 112. In an exemplary embodiment, the thickness of porous coating 912 can be between about 25 μm and about 800 μm thick. The substrate 910 can be any polymeric material, such as PEEK, Polymethyl Methacrylate (PMMA), or any other biocompatible polymer with a Young's modulus between about 0.1 GPa and about 50 GPa, which may be used as the interbody spacer 100. The porous coating 912 is constructed from an osteoconductive material, such as titanium, nickel titanium, or any other material which may encourage bone in growth. The porous coating 912 is rigidly bounded to substrate 910 through a bonded layer 911, such as by a plasma spray, vapor deposition, or another other surface additive method. The pores in substrate 912 contains small to large size cavities 914, which encourage bone in-growth and attachment. In an exemplary embodiment, the porosity of the pores substrate 912 can be between about 5 percent and about 80 percent porous. The interbody spacer 100 superior dome 412 and superior surface 116 are coated with the porous coating 912, as is the inferior dome 711 and inferior surfaces 117. The coating allows the interbody spacer rigid body 111 to maintain the low stiffness, which can be constructed from PEEK or low stiffness polymer, while gaining the porous coating 912 with osteoconductive properties.

Optionally, a hydroxyapatite coating can be applied on surfaces 113, 114, 115 and on the walls of cavity 118 to enhance for visualization of implant 100 after implementation.

Another embodiment of the invention is the insertion instrument 1000 illustrated in FIGS. 10-14, which is used to insert interbody 100 into the spine. The insertion instrument 1000 must capture the interbody spacer 100, position the interbody spacer 100, and deploy the interbody spacer 100 in between two adjacent vertebral bodies (not shown). The insertion instrument 1000 has a handle 1010 used to grip the instrument and rear end 1020 that can cooperate with an impact device (not shown). The hollow shaft 1016 is of a smaller diameter than the handle and has enough length to maneuver around soft tissue. Located between the shaft 1016 and handle 1010 has a cam 1018 used to engage and disengage a drive shaft 1252 from the aperture 119 in the interbody spacer 100. A fastener portion, or engagement end 1014, is located at the opposite end from the rear end 1020.

Figure 11:
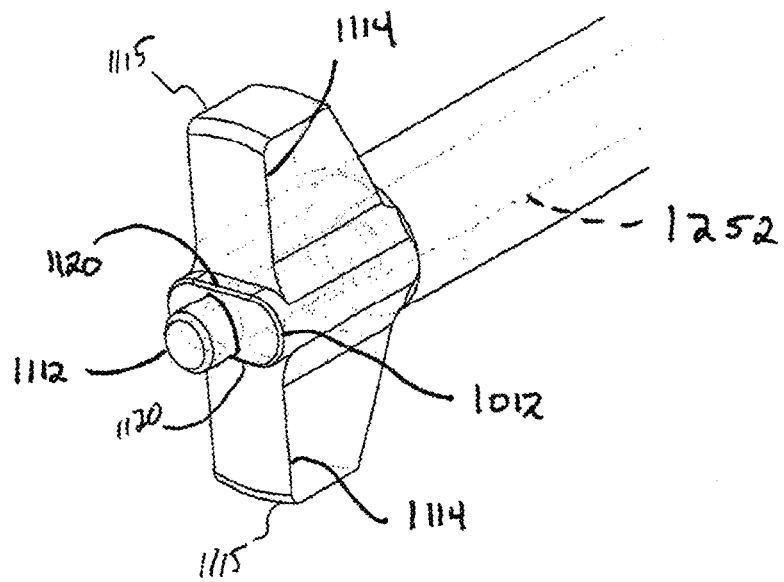
FIG. 11 is an enlarged perspective view of an insertion instrument of FIG. 10, engagement end.
Figure 12A:
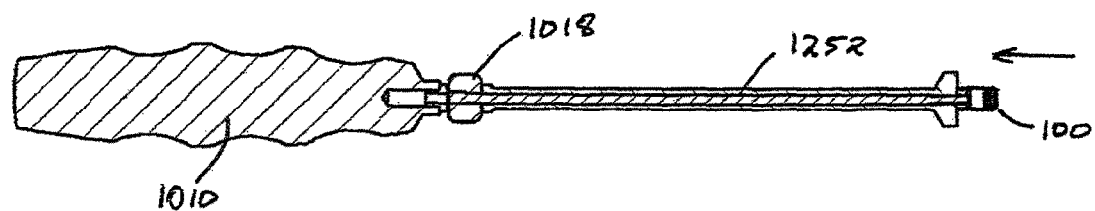
FIG. 12(a) is a cross section view of the insertion instrument of FIG. 10, showing the attachment mechanism.
Figure 12B:
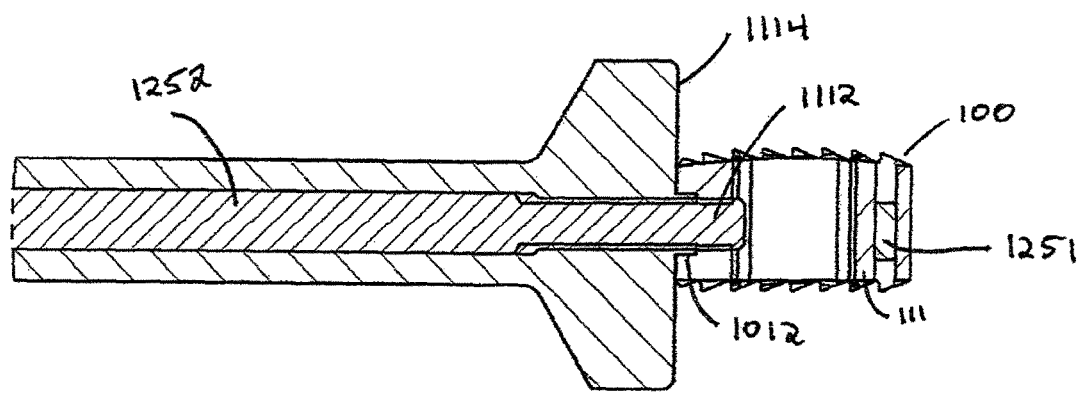
FIG. 12(b) is an enlarged truncated cross section view of the insertion instrument implant attachment of FIG. 10.

The engagement end 1014 is illustrated in FIGS. 11-12b and is designed to releasably engage the interbody spacer 100. The engagement end 1014 contains an engagement extension 1112, which is located at the end of the drive shaft 1252. The engagement extension 1112 is centrally located within the congruent extension 1012, which is defined by two parallel edges 1120. The congruent extension 1012 must contain at least one parallel edge 1114 but can be in a circular, rectangular, hexagonal, triangular or oblong. The engagement end 1014 may also have depth stop 1115, which is used to control the placement of the interbody spacer 100 within the intervertebral disc space. The height of the depth stops 1115 must be greater than the highest interbody spacer 100.

Figure 13:
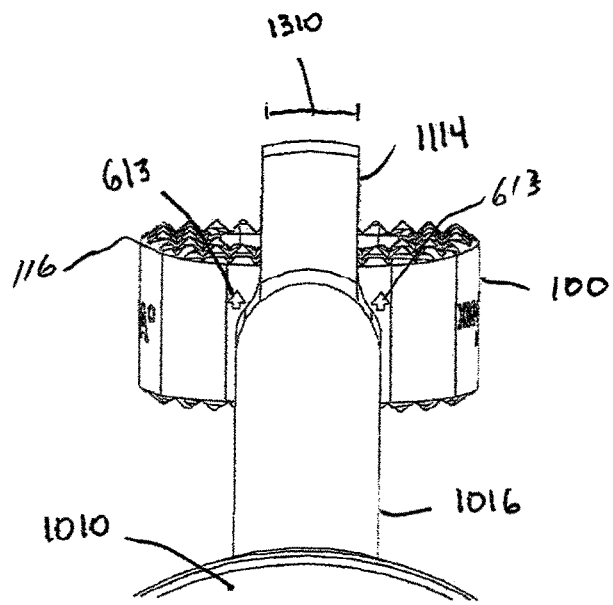
FIG. 13 is an enlarged axial view of the insertion instrument of FIG. 10, showing visualization of the alignment features.
Figure 14:
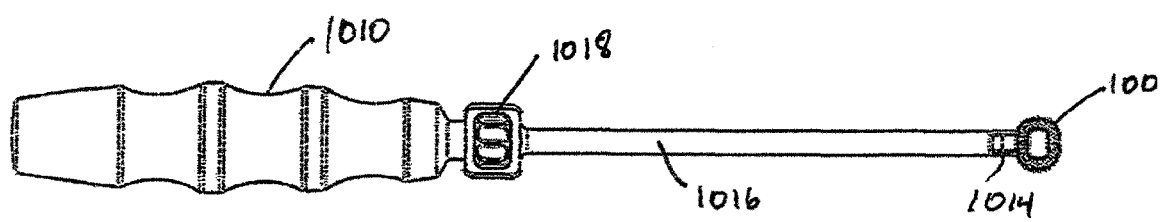
FIG. 14 is a top of view of the insertion instrument of FIG. 10.

FIGS. 12-14 illustrate the attachment of the interbody spacer 100 to the insertion instrument 1000. The interbody spacer 100 is positioned at the engagement end 1014 of the insertion instrument 1000. The engagement extension 1112 is coaxially aligned with and inserted into the implant aperture 119 in the recess 120 and the cam 1018 is rotated. The cam 1018 translates rotational motion through the drive shaft 1252 and extends engagement extension 1112, until engagement is achieved. In this example, the engagement extension 1112 and aperture 119 have matching threads, however engagement may also be completed by an interference fit or other suitable engagement means. The rotation of the cam 1018 draws the interbody spacer 100 until contact is achieved with depth stops 1115. The interbody spacer 100 is then placed into position by using an impaction device (not shown), such as, for example, a mallet, a hammer, a slap hammer, or other such device, on the rear end 1020 until the depth stops 1114 are flush with the surface of the vertebral bodies (not shown). The cam 1018 is then rotated in the reverse (unlocking) direction to retract engagement extension 1112 inwardly into shaft 1016 in the direction of arrow "A" in FIG. 12a, and the engagement extension 1112 is then removed from interbody spacer 100. In the case of the non-symmetric interbody spacer, alignments to the proper direction of the spine is important, as shown in FIG. 13. In this case, indicator arrows 613 point towards the superior surface 116 and superior dome 412. During insertion, the surgeon needs to visualize these indicator arrows 613 and the insertion instrument 1000 depth stop 1115 must have a width 1310 small enough to visualize the arrows 613.

Another embodiment of the invention is a plate assembly 1500 illustrated in FIGS. 15-22. The plate assembly 1500 contains a rigid body 1508, which is defined by anterior surface 1510, posterior surface 1512, and an external perimeter 1518. The plate has a generally "dog bone" shape but can have a rectangular, square or triangular shape. In an exemplary embodiment, the plate 1500 includes at least two screw recesses 1520. Located in the center of the plate is a generally frusto-conical countersunk surface 1542 and attachment aperture 1540. The attachment aperture 1540 is designed to align coaxially with the interbody spacer 100 aperture 119 and has an equal or larger diameter than aperture 119. The countersunk surface 1542 and attachment aperture 1540 are coaxially aligned with the congruent extension 1012. The attachment aperture 1540 is shown with a circular configuration but could be an oblong or oval shape to allow linear translation of a locking screw 1810 (shown in FIG. 18) relative to the plate 1500.

Figure 16:
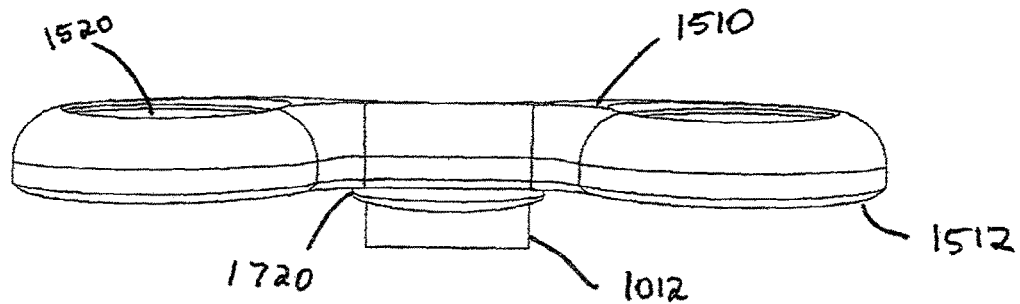
FIG. 16 is a side view of the implant of FIG. 15.
Figure 17:
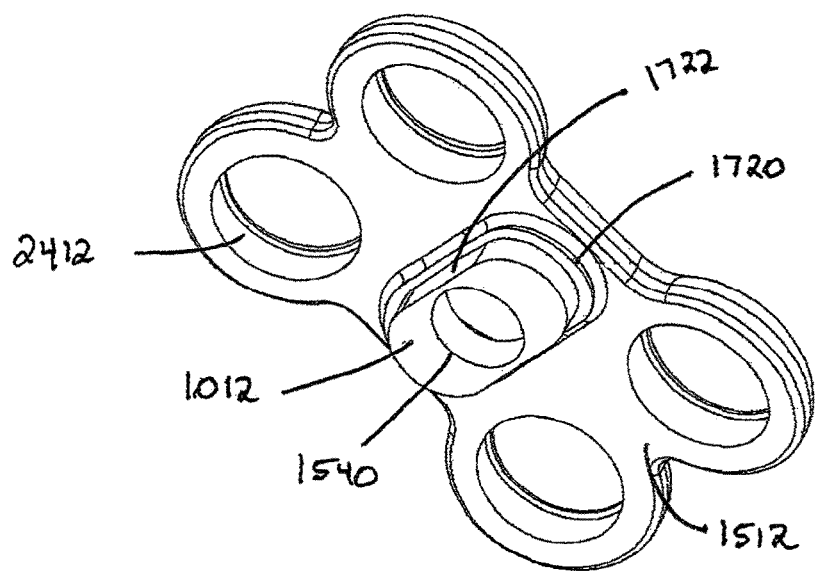
FIG. 17 is a perspective view of a plate's posterior side showing rectangular connection of the plate shown in FIG. 15.

FIGS. 16-17 show a side view and bottom view of a congruent extension 1012, respectively. The congruent extension 1012 is located on the posterior side 1512 of the plate assembly 1500 and is designed to engage with a recess 120, such as the one contained on the interbody spacer 100. The interbody spacer 100 is designed to sit in the center of plate assembly 1500. As such, the interbody 100 may be recessed beneath the vertebral walls. Therefore, the congruent extension 1012 sits on a congruent extension shelf 1720. The mating side of the congruent extension shelf 1720 matches the surface of the implant, such as the anterior surface 113 of the interbody spacer 100. In order to block rotation of the plate 1500, the congruent extension 1012 contains at least one straight portion 1722 that engages parallel edge 312, which may be incorporated into a circle, square, rectangle, triangle or oblong shape.

Figure 18:
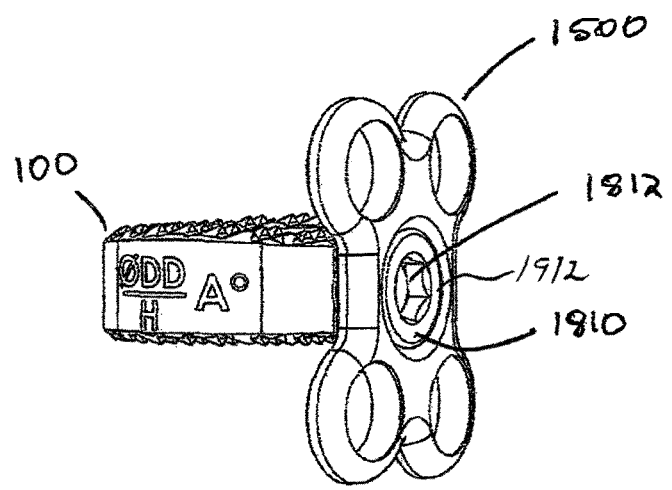
FIG. 18 is a perspective view of the plate shown in FIG. 15, attached to intervertebral implant of FIG. 1, with attachment mechanism.
Figure 19:
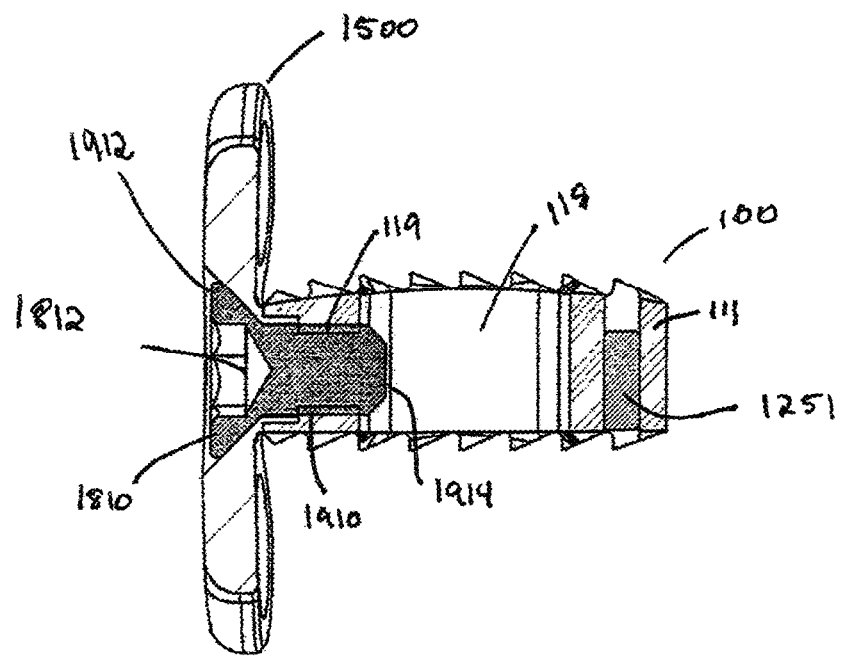
FIG. 19 is a side cross section view of the plate and intervertebral implant assembly of FIG. 18, showing connection means.
Figure 20:
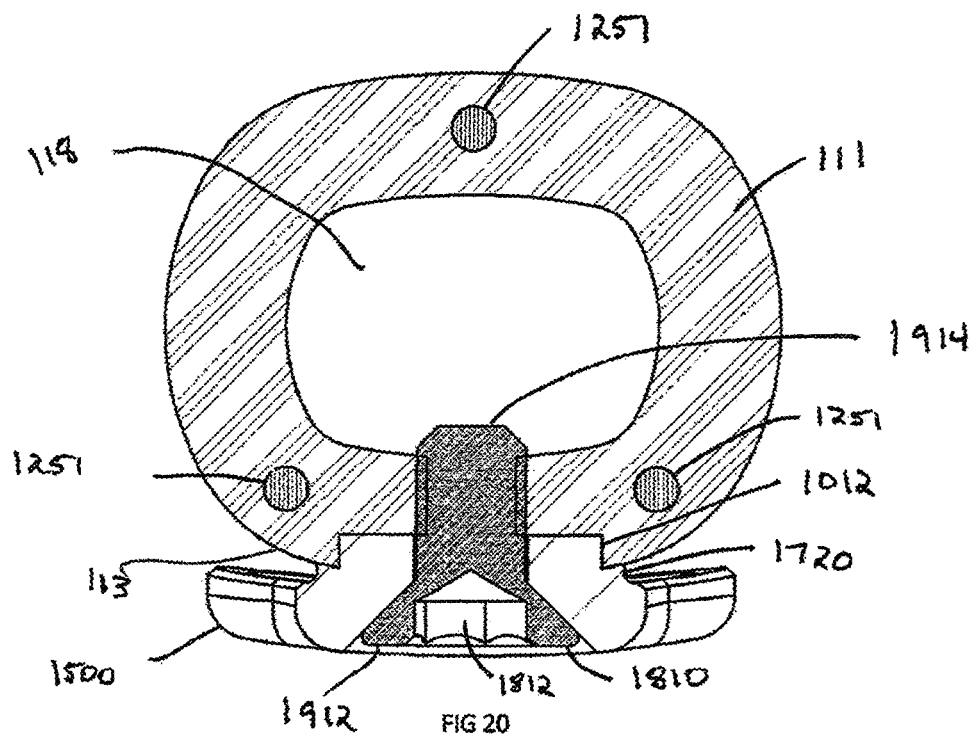
FIG. 20 is a top cross section view of the plate and intervertebral implant assembly of FIG. 18, showing connection means.

The congruent extension 1012 cooperatively engages the recess 112 of the interbody spacer 100, as illustrated in FIGS. 18-20. Once the congruent extension 1012 is seated in the recess 120 of interbody spacer 100, locking screw 1810 can be used to secure the plate assembly 1500 to the interbody 100. The locking screw 1810 generally has instrument recess 1812 on the head 1912 and threads on the shaft 1910. The instrument recess 1812 is shown with a hexagonal connection but those skilled in the art will recognize that the connection can be a Torx, Philips, Square or any other torque transmitting connection. The locking screw 1810 has sufficient length for the trailing end 1914 to remain slightly recessed or extend in the central opening 118. In the example shown, the shaft 1910 is threaded into the aperture 119 in the interbody spacer 100; however this can be an interference fit or any other fit in which the locking screw 1810 cannot disengage from the interbody spacer 100.

Figure 21:
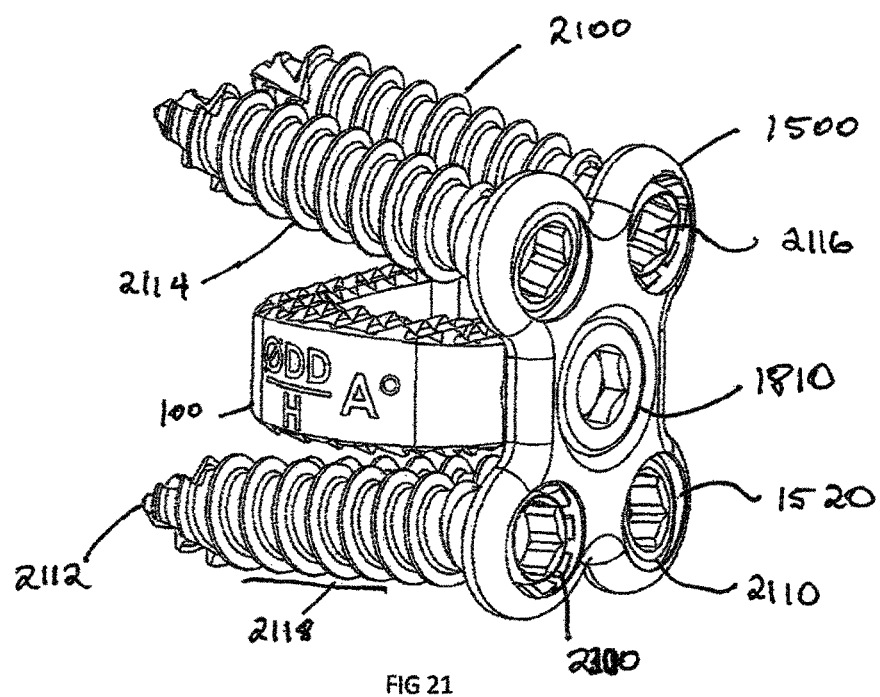
FIG. 21 is a perspective view of a fully configured plate and intervertebral implant, shown in FIG. 18, with bone screws, in accordance with another exemplary embodiment of the invention.
Figure 22:
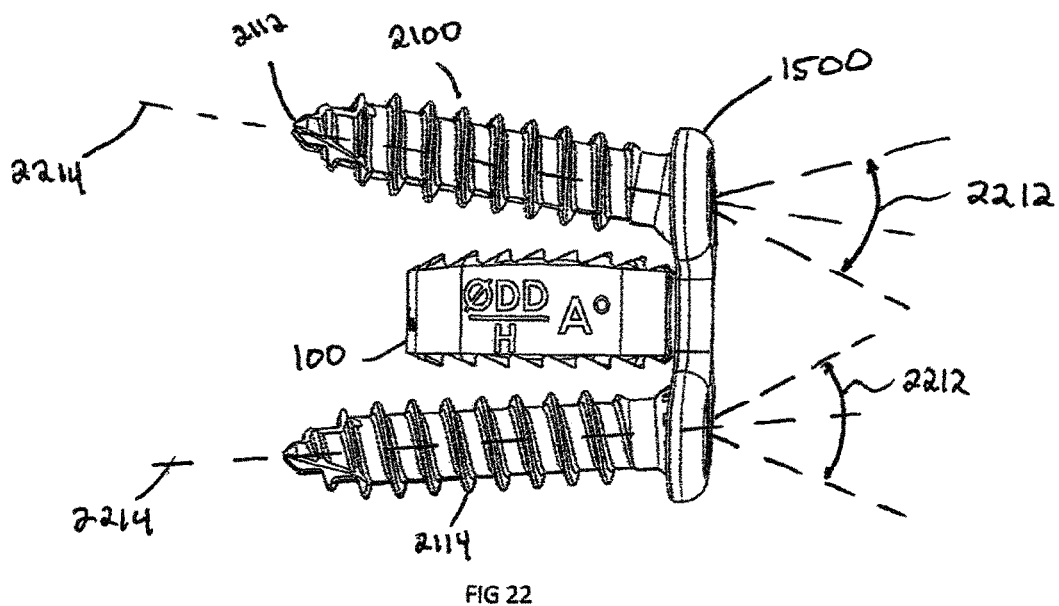
FIG. 22 is a side view of the fully configured plate and intervertebral implant assembly of FIG. 21.
Figure 23:
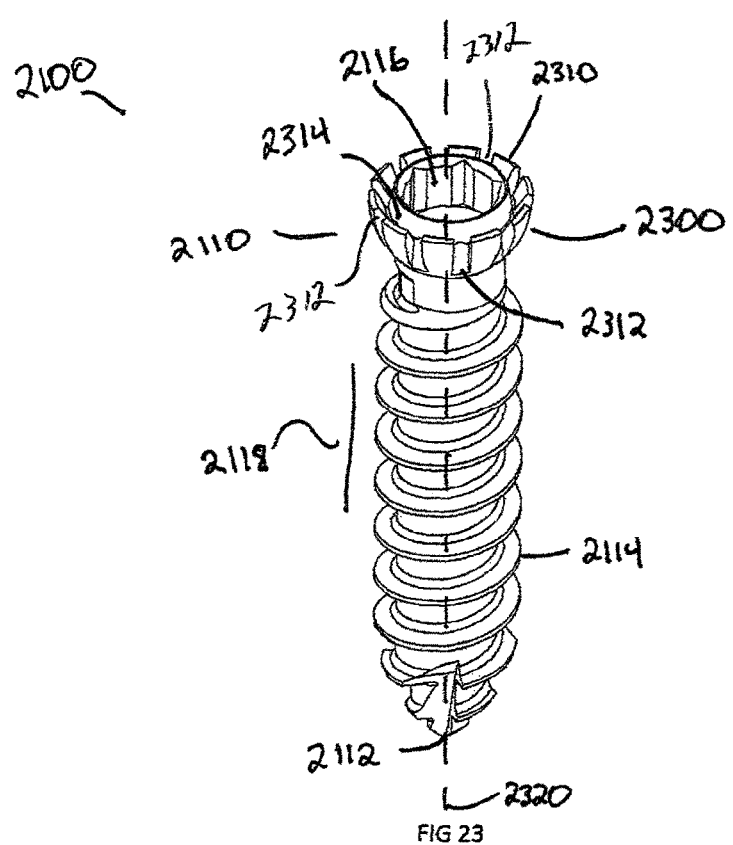
FIG. 23 is a perspective view of a fifth exemplary embodiment, showing a bone screw with cantilever segments.

FIGS. 21 and 22 illustrate the attachment of bone screw 2100 to the plate assembly 1500 and interbody spacer 100. As shown in the Figures, when the plate 1500 is coupled to the intervertebral implant 100, a first plurality of the recesses 1520 extends above the upper surface of implant 100 and a second plurality of recesses 1512 extends below the lower surface of the implant 100. The combination of the bone screws 2100 in the plate assembly 1500 and interbody spacer 100 is to prevent motion post-operatively to enable the vertebral bodies to fuse to the porous coating 912 of interbody spacer 100 and achieve bone growth through the central opening 118. Referring to FIG. 23, the bone screws 2100 have a bulbous head 2110 and a head recess 2116 designed for engaging a mechanical translating instrument, such as a screw driver. The shaft 2118 is composed of a plurality of bone threads 2114 and terminate at a distal end 2112. The distal end 2112 is configured to self-drill and tap into the bone with the use of minimal instrumentation.

The plate assembly 1500 screw recess 1520 is designed with a spherical seat 2412 (shown in FIG. 24) to allow the bulbous head 2110 to seat in a variety of angular positions based of on an angle 2212 (shown in FIG. 22) from the center axis 2214 of the plate assembly 1500. The angle 2212 allows for the surgeon to customize the position of the bone screw 2100 intraoperatively. The spherical like shape of the bulbous head 2110 allows for the bone screws 1500 to adapt as the vertebral endplates settle on the superior surface 116 and inferior surface 117 of the interbody spacer 100. This plate configuration is known as semi-constrained; however the bone screw recess 1520 could be slotted to allow for linear dynamic transition of the bulbous head 2110.

Another embodiment of the invention is the locking head 2300 of bone screw 2100 further illustrated in FIG. 23. The locking head 2300 is composed of a plurality of cantilever segments 2310 extending around the head 2300 that are created when a circular groove 2314 is segmented by a plurality of gaps 2312 at equal distance from each other. In order for the cantilever segments 2310 to deform, at least one gap 2312 must be created between them. The groove 2314 is created circumferentially around the axis 2320 of bone screw 2100 and extends outwards from the head recess 2116.

Figure 24:
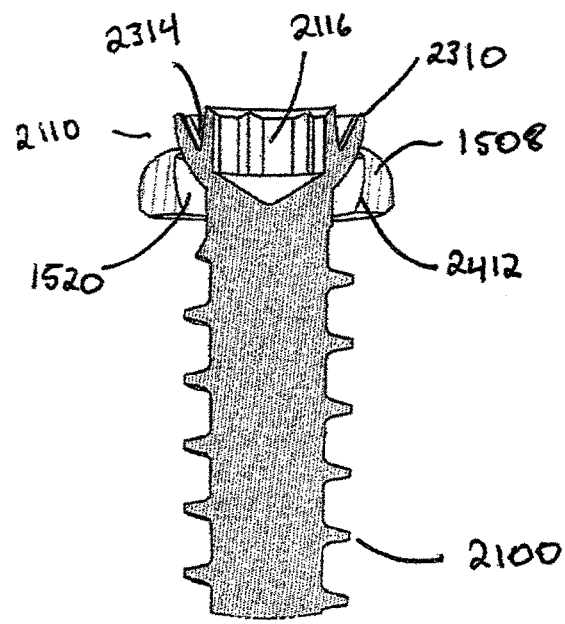
FIG. 24 is a truncated cross section view of the bone screw shown in FIG. 23, inserted into the plate shown in FIG. 15, in a non-locked state.
Figure 25:
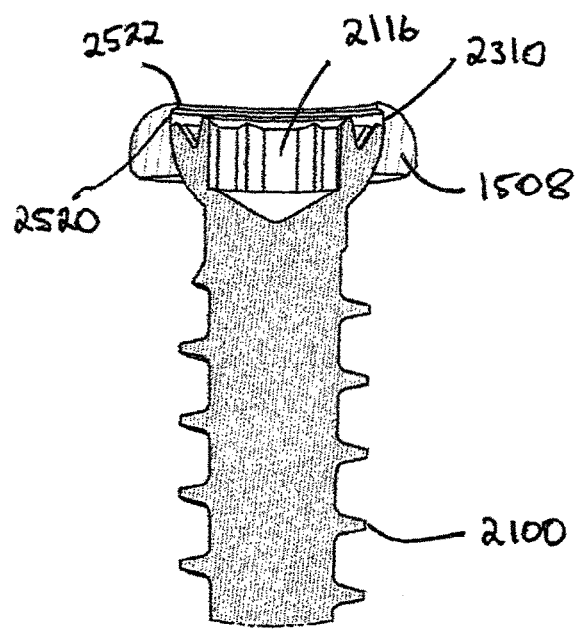
FIG. 25 is a truncated cross section view of the bone screw of FIG. 23, inserted into the plate shown in FIG. 15, in a locked state.
Figure 26:
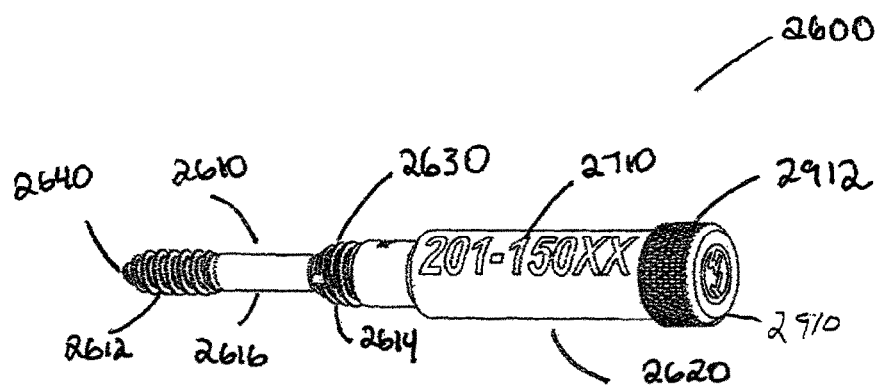
FIG. 26 is a perspective view of a sixth exemplary embodiment, showing a bone screw with removable body extension.
Figure 27A:
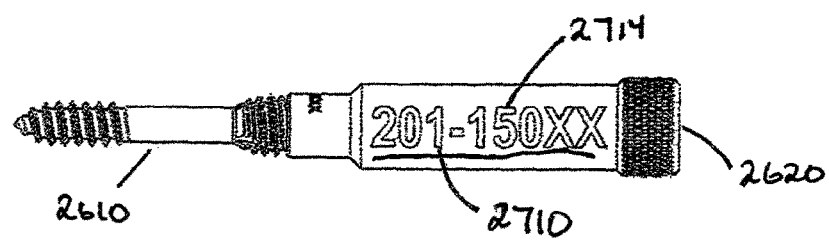
FIG. 27(a) is a side view of a bone screw with removal body extension shown in FIG. 26, showing descriptive information.
Figure 27B:
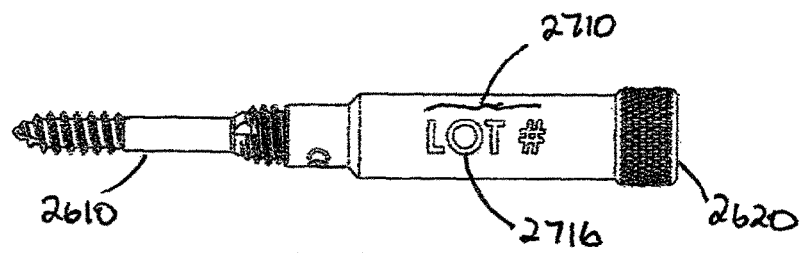
FIG. 27(b) is a further rotated side view of a bone screw with removal body extension shown in FIG. 26, showing descriptive information.
Figure 28:
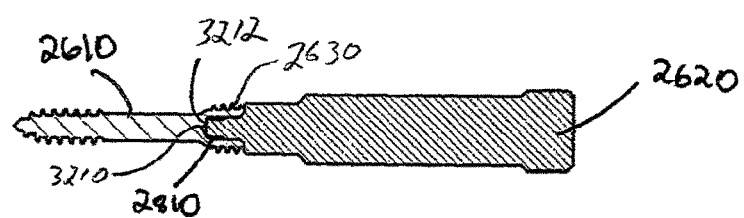
FIG. 28 is a cross section view of bone screw with removal body extension shown in FIG. 26.
Figure 29:
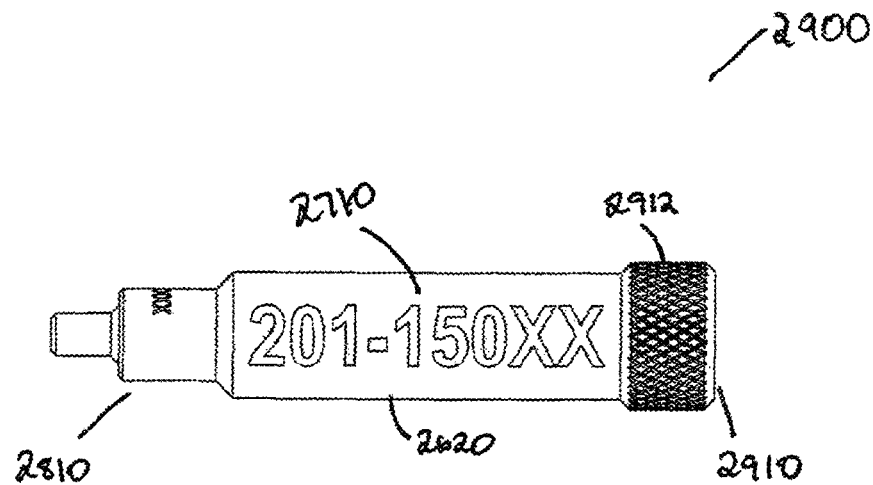
FIG. 29 is a side view of a removal body extension showing descriptive information.

FIGS. 24 and 25 show the bone screw 2100 inserted into a rigid plate body 1508 in an unlocked and locked position, respectively. The rigid body 1508 screw recess 1520 is designed to have a spherical seat 2412, an undercut ledge 2520, and a cylindrical section 2522 extending inwardly from the ledge 2520. The spherical seat 2412 is designed to cooperatively engage the bone screws bulbous head 2110 while allowing translation about the bone screw bore center axis 2214. The cantilever segments 2310 are designed to deflect, or bias, inwardly during insertion of the bone screw 2100 in the screw recess 1520 by contacting the cylindrical section 2522 and deflecting towards the bone screw axis 2320. The deflection is great enough to allow the bulbous head 2110 to pass, but not enough to plastically deform the cantilever segments 2310. Once the bulbous head 2110 has passed the cylindrical section 2522 the cantilever segments 2310 elastically spring back, or bias outwardly beneath cylindrical section 2522. The undercut ledge 2520 prevents the bone screws 2100 from disengaging from the plate 1508. The undercut ledge 2520 also blocks excessive rotation of the bulbous head 2110 but contacts the top of the cantilever segment 2310.

Another exemplary embodiment of the invention is a removable body extension assembly 2600 as illustrated in FIGS. 26-30. The removable body extension assembly 2600 is a cylindrical shaped extension, which can be attached to a headless bone screw 2610, bone screw 2100, plate 1500, or any other implantable implant requiring UDI tracking. The removable body extension assembly 2600 allows for indicia, or descriptive information 2710, such as the part number 2714 and or serial/lot number 2716, to be contained with the implant, specifically, when the surface area, like the shaft 2616 of screw 2610, is not large enough to contain the descriptive information 2710.

The removable body extension assembly 2600 has an engagement end 2810 specifically designed to interface with an implant. In the example shown in FIG. 28, the engagement extension 2810 is threaded to engage recess 3212 in the proximal head 2630 of a headless compression bone screw 2610. The engagement extension 2810 can be press fit or have an interference fit engagement recess 3212 or head recess 3210 of the implant. The engagement extension 2810 may also be manufactured directly as part of the implant in a monolithic configuration and disengage through breaking connection located at the engagement extension end 2810.

In the case of the headless compression screw 2610, one issue during surgery is removing the headless compression screw 2610 from a screw holder because of the sharp proximal threads 2614 located on the proximal head 2630. The proximal end 2910 of the removable body extension 2600 can be smooth or knurled to allow a grip zone 2912. Prior to inserting headless compression screw 2610, the removable body extension 2900 is used to remove the screw from a screw caddie (not shown). The removable body extension 2900 is then removed by unscrewing the engagement section 2810 from the engagement recess 3212 of screw 2610. Screw 2610 is then inserted into the patient. The removable body extension 2900 is left outside of the patient and the descriptive information 2710 is recorded.

Figure 30:
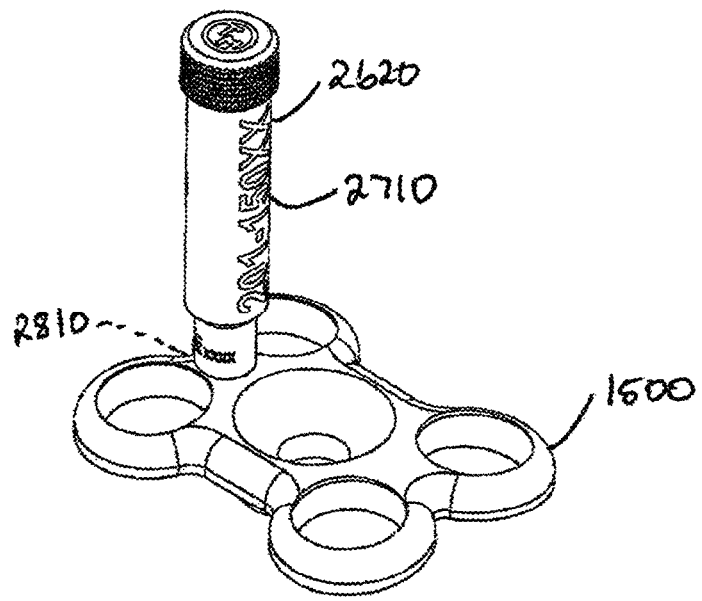
FIG. 30 is a perspective view showing the removable body extension of FIG. 29, attached to the plate shown in FIG. 15.
Figure 31:
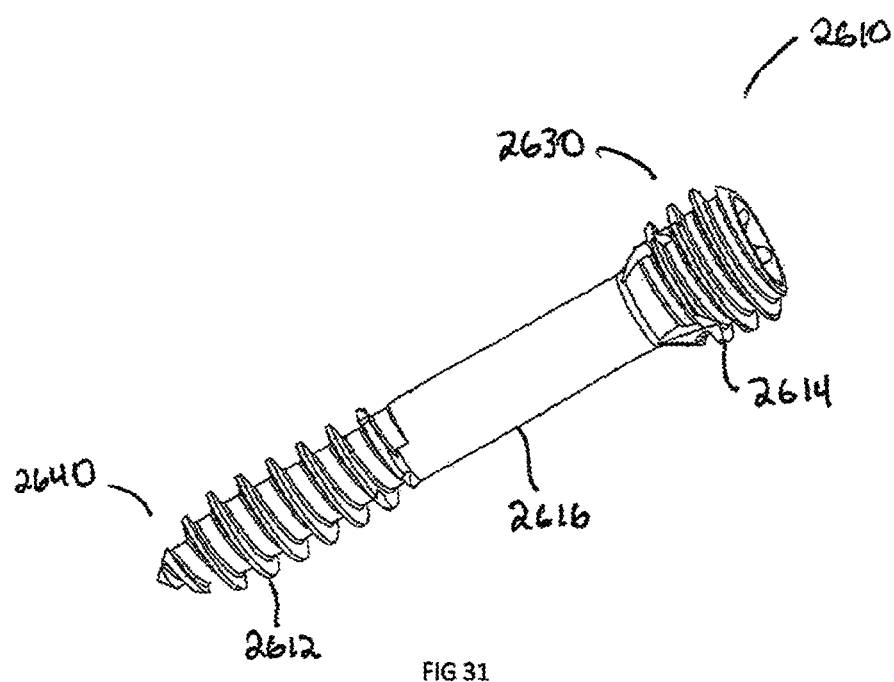
FIG. 31 is a perspective view of a sixth exemplary embodiment, showing a bone screw.
Figure 32:
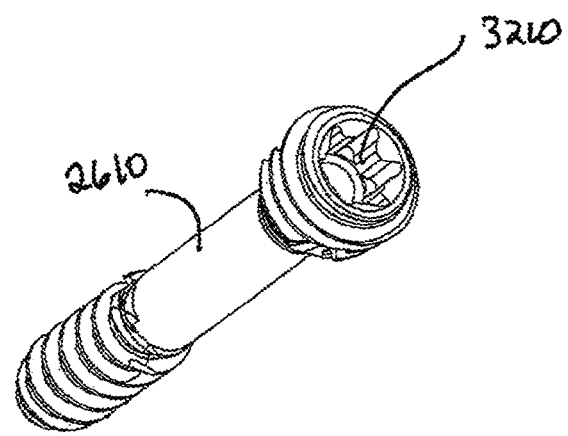
FIG. 32 is another perspective view of the bone screw shown in FIG. 31.
Figure 33:
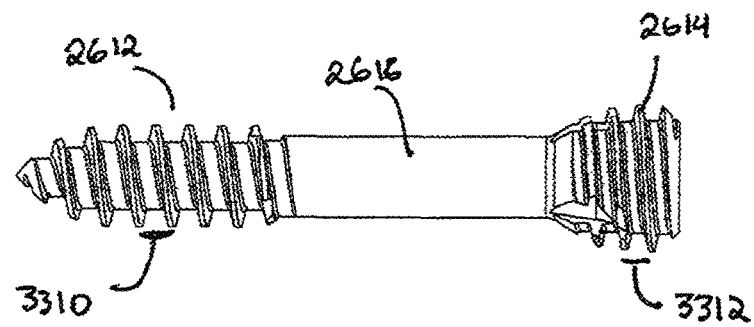
FIG. 33 is another side view of the showing a bone screw shown in FIG. 31.
Figure 34:
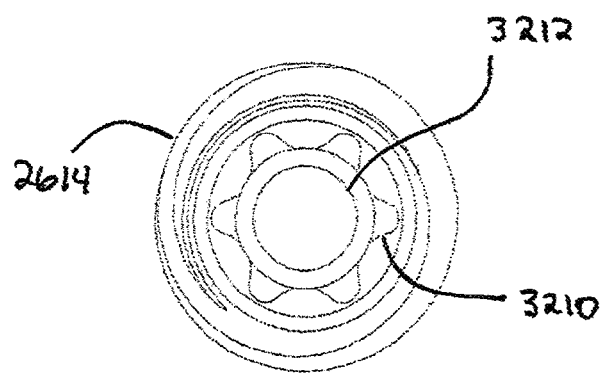
FIG. 34 is a top view showing the bone screw of FIG. 31.
Figure 35:
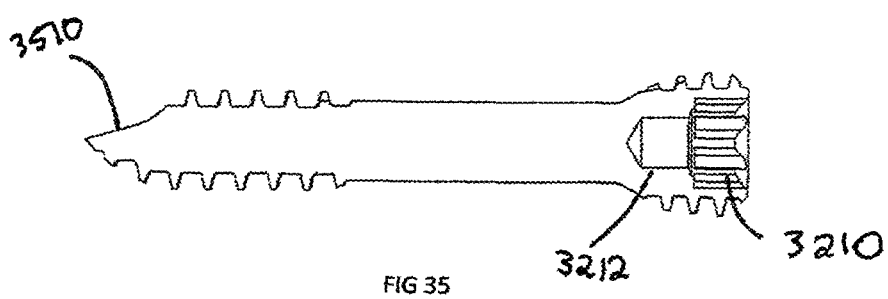
FIG. 35 is a cross sectional view showing the bone screw shown in FIG. 31.

In addition to headless bone screws, FIG. 30 shows an example of a plate 1500 with the removable body extension 2900 attached via the engagement extension 2810. The removable body extension 2900 can be attached to a number of implants, such as the interbody spacer 100, plate 1500, headless compression screw 2610, bone staple (not shown), suture anchor (not shown), or any other implant which is too small to physically laser mark descriptive information 2710. In another embodiment shown in FIGS. 31-38, headless compression screw 2610 is shown in more detail. The headless compression screw 2610 is defined by proximal head 2630 and a distal end 2640 joined by a shaft 2616. The distal end 2640 has distal threads 2612 with a distal pitch 3310 and the proximal head 2630 has proximal threads 2614 with a proximal thread pitch 3312, where the proximal thread pitch 3312 is less than distal thread pitch 3310. The difference in proximal thread pitch 3312 and distal thread pitch 3310 causes a compressive force to generate between segments. The proximal head 2630 has an engagement recess 3210 which can be a Torx, Hexagonal, Square, or Phillips in shape.

Figure 36:
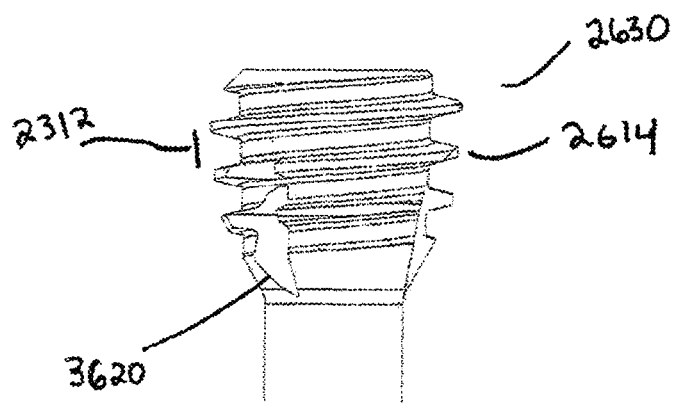
FIG. 36 is an enlarged view of the proximal end of the bone screw shown in FIG. 31.
Figure 37:
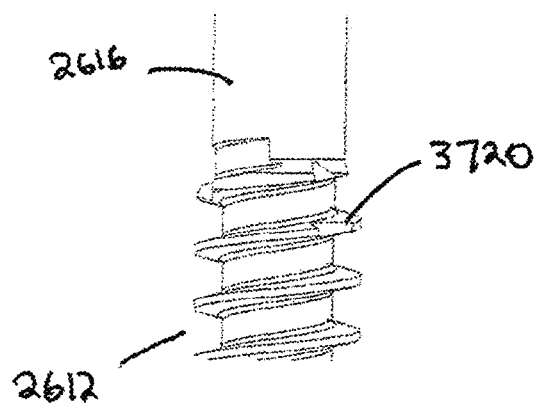
FIG. 37 is an enlarged view of the shaft of the bone screw shown in FIG. 31.
Figure 38:
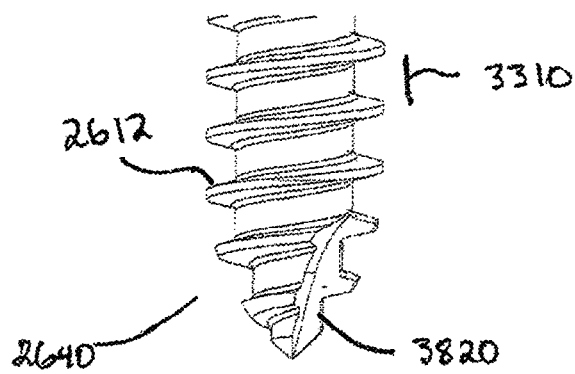
FIG. 38 is an enlarged view of the distal end of the bone screw shown in FIG. 31.
Figure 39:
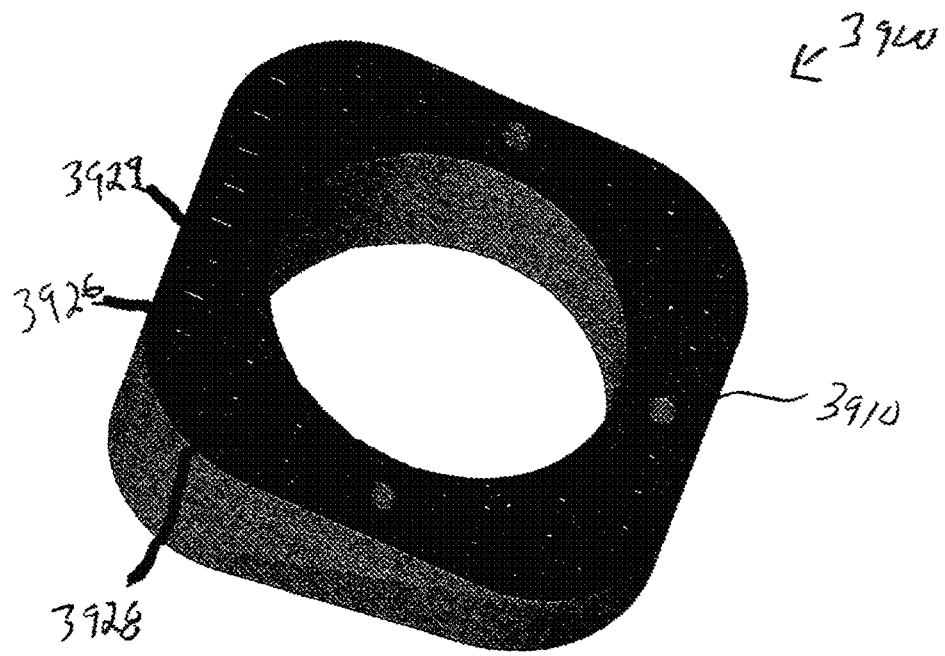
FIG. 39 is a perspective view of an osteotomy implant according to an exemplary embodiment of the present invention.
Figure 40:
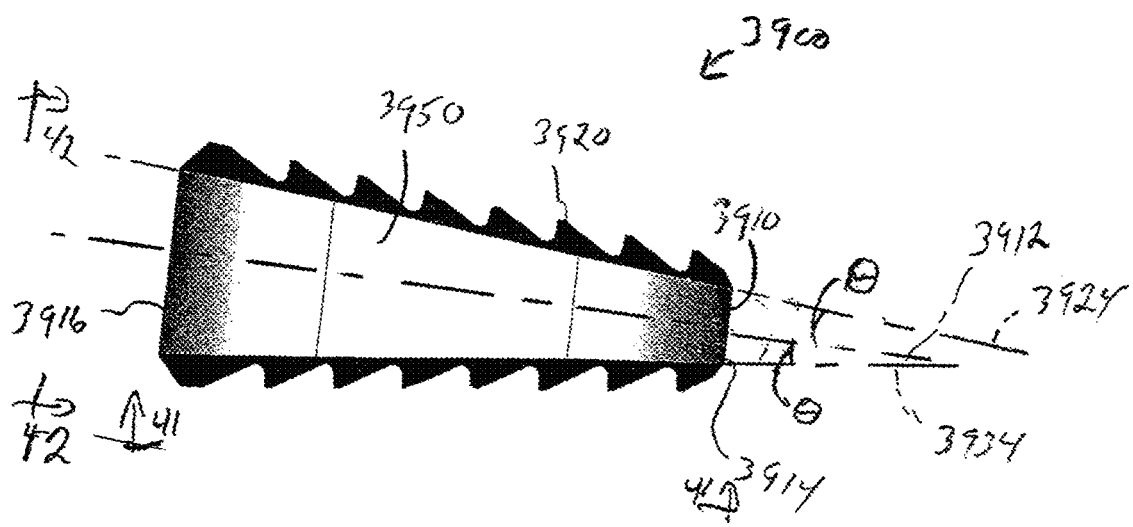
FIG. 40 is a side elevational view of the osteotomy implant shown in FIG. 39.

FIGS. 36-38 specifically show the self-cutting features of the headless bone screw 2620. The proximal head 2630 has a groove 3620, which removes material as the proximal head 2630 and the proximal threads 2614 begin to engage a substrate, such as bone.

FIG. 37 illustrates a reverse cutting groove 3720 positioned on the distal end 2640 and engages the distal threads 2612 near the shaft 2616. The reverse cutting groove 3720 removes material, such as bone, as the headless bone screw 2610 is removed.

FIG. 38 illustrates the tip of the distal end 2640, which includes distal threads 2612 and self drilling groove 3820. The length of self-drilling groove 3820 is greater than the distal thread pitch 3310 and is used as the headless bone screw 2610 is inserted into a substrate such as bone.

In an alternative embodiment of the present invention, shown in FIGS. 39-44 an osteotomy wedge system according to the present invention is disclosed. The wedge system can be used for internal fixation of bone fractures, fusions, or osteotomies in lower limbs, such as, for example, tibial osteotomies, Evans osteotomies, metatarsal/cuneiform arthrodesis, Cotton osteotomies, as well as other indications.

The inventive wedge system provides a fusion site for bone to grow into an osteotomy wedge to secure the wedge into an incision that is formed in the bone into which the wedge is inserted. The wedge helps to stabilize the bone and to properly orient the bone. The fusion site secures the wedge to the bone as the bone continues to grow.

Figure 41:
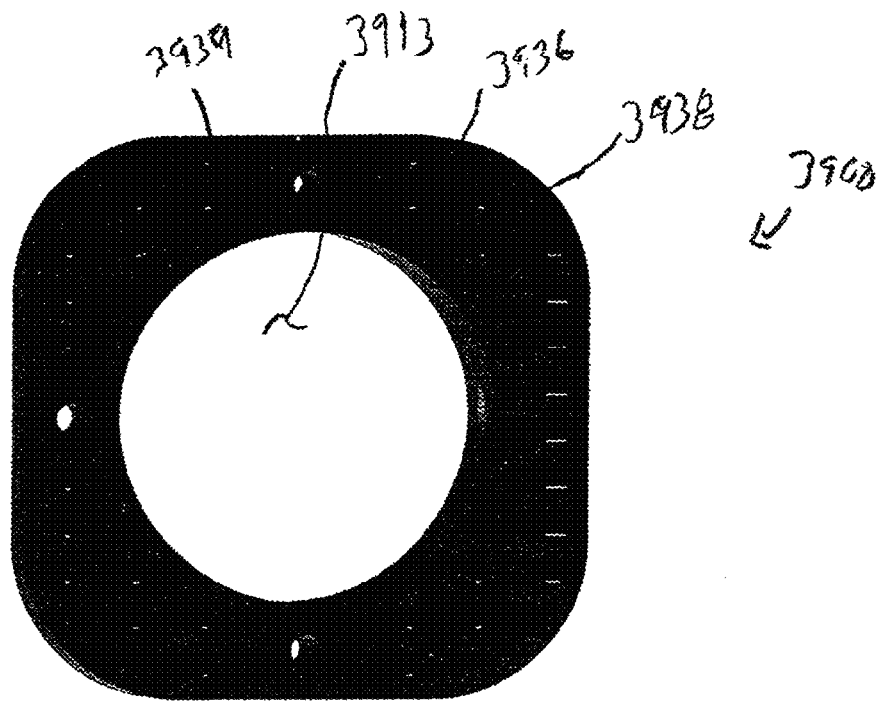
FIG. 41 is a bottom plan view of the osteotomy implant shown in FIG. 40, taken along lines 41-41 FIG. 40.

Referring to FIGS. 39-42, the wedge system includes a wedge 3900 having a body 3910 that is generally bisected by a central plane 3912. A top plan view of body 3910, shown in FIG. 41, shows that body 3910 is generally parallelogram in shape with rounded corners and has a generally circular opening 3913 extending all of the way therethrough. Circular opening 3913 provides for bone through growth to occur.

Body 3910 is generally wedge-shaped with a thinner central portion 3914 sized to be inserted toward an interior portion of a cut bone 50, and a wider peripheral portion 3916, forming a trailing face that is sized to extend toward an exterior of the cut bone 50. Body 3910 includes a first surface 3920, an opposing second surface 3930, and a core 3950 disposed between first surface 3920 and a second surface 3930.

A first surface 3920 extends between medial portion 3914 and lateral portion 3916 generally in a first plane 3924 that extends obliquely at an acute angle θ relative to central plane 3912. First surface 3920 has a first plurality of longitudinal grooves 3926 and a second plurality of transverse grooves 3928 extending therealong. Portions of first surface 3920 extend between adjacent longitudinal grooves 3926 and transverse grooves 3928 form individual peaks 3929, similar to the surface of interbody spacer 100, shown in FIGS. 1-3.

Similarly, a second surface 3930 extends between medial portion 3914 and lateral portion 3916 generally in a second plane 3934 on an opposite side of central plane 3912 from first surface 3920, also at an acute angle θ relative to central plane 3912. Second surface 3930 has a first plurality of longitudinal grooves 3936 and a second plurality of transverse grooves 3938 extending therealong. Portions of second surface 3930 extend between adjacent longitudinal grooves 3936 and transverse grooves 3938 form individual peaks 3939.

Each of first surface 3920 and second surface 3930 includes a osteoconductive coating, such as, for example, a titanium plasma spray coating, that has a thickness of between about 2 microns and about 500 microns. The osteoconductive coating can be used to add peripheral visualization within minimal imaging artifact. The spray coating is sufficiently thin, such that first surface 3920 and second surface 3930 do not interfere with imaging methods, and are therefore largely transparent to imagery. Alternatively, the spray coating can be sufficiently thick to enable peripheral visibility of first surface 3920 and second surface 3930 without affecting the visibility of core 3950 via imaging, in order to allow the progress of bone growth to be viewed.

First surface 3920 and second surface 3930 can each be a highly roughened exterior surface to provide an environment conducive to early stability and to ensure intimate osseointegration between bone 50 (shown in FIGS. 43 and 44) and implant 3900. The roughened surface has an Ra greater than 0.006 microns.

Figure 42:
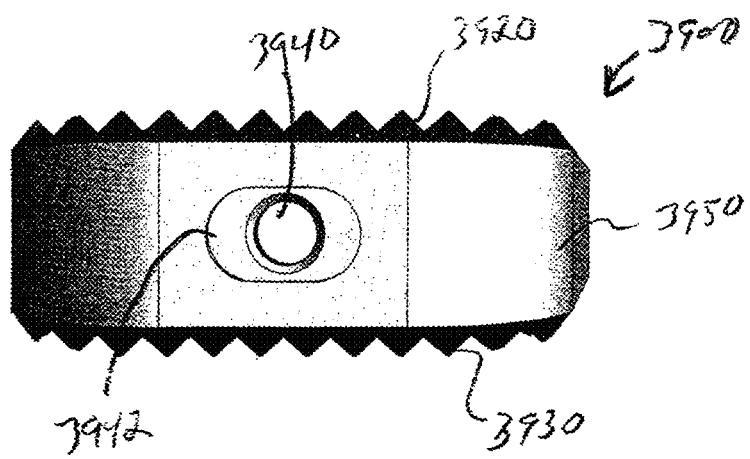
FIG. 42 is a lateral side elevational view of the osteotomy implant shown in FIG. 40, taken along lines 42-42 of FIG. 40.
Figure 13:
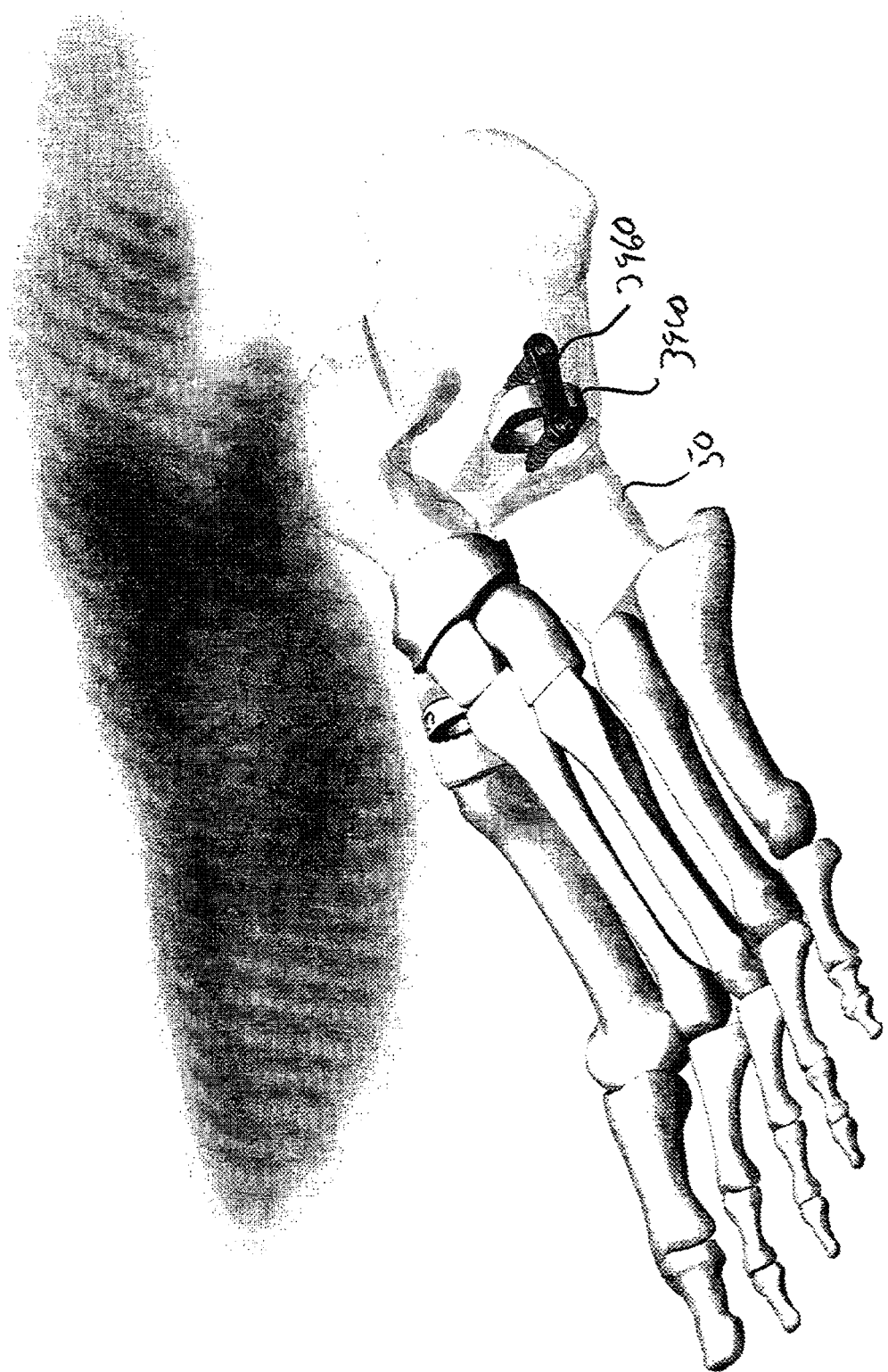

In an exemplary embodiment, core 3950 can be constructed from a radiolucent material, such as, for example, PEEK, and is transparent on MRI, CT, and x-ray imaging. Core 3950 has the same Young's modulus as bone, namely, about 3.6 GigaPascals (GPa), which prevent shielding in bone 50, while also maintaining superior mechanical properties. In an exemplary embodiment, core 3950 having a Young's modulus between about 0.5 GPa and about 18 GPa can be used. FIG. 9 shows a PEEK core with an osteoconductive (titanium plasma spray) surface As shown in FIG. 42, lateral portion 3916 includes an aperture 3940 that is centrally located within a recess 3942 between first surface 3920 and second surface 3930. Aperture 3940 can be configured in either a threaded configuration, interference configuration or any means to secure the body 3910 to a separate insertion instrument 1000 (shown in FIG. 14). In the embodiment of wedge 3900 shown in FIG. 42, aperture 3940 has blind threads.

In the exemplary embodiment shown FIG. 42, recess 3942 is generally oblong in shape to prevent rotation of implant 3900 respect to insertion instrument 1000 implantation of implant 3900 into bone 50.

Figure 44:
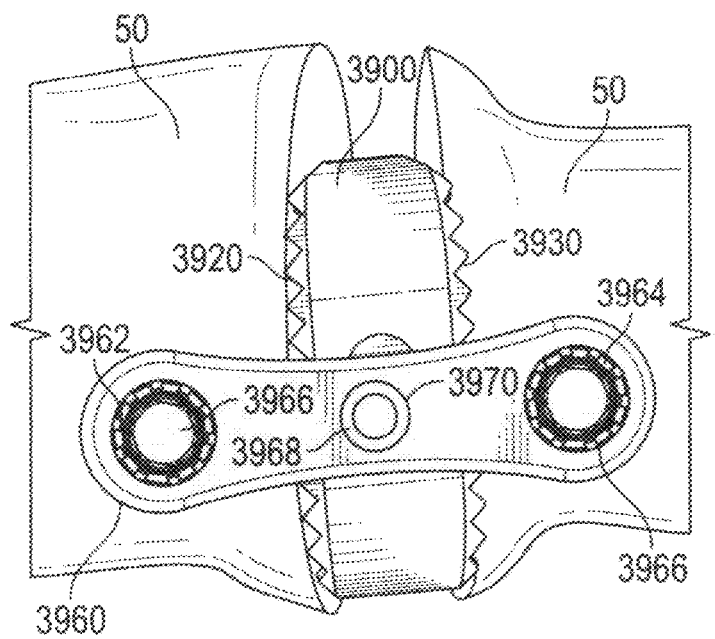
FIG. 44 is an enlarged lateral side elevational view of the osteotomy implant shown in FIG. 43.
Figure 45:
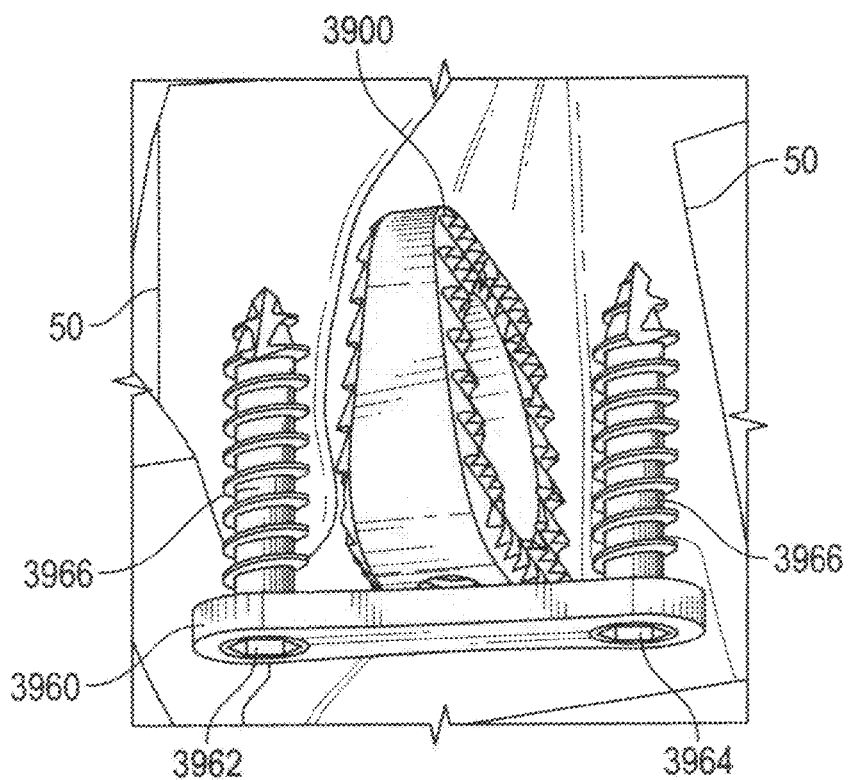
FIG. 45 is an enlarged top plan view of the osteotomy implant and faceplate shown in FIG. 43.

As shown in FIGS. 43-45, the inventive osteotomy wedge system further includes a fixation plate 3960 that is attached to bone 50 over wedge 3900 after wedge 3900 is inserted into bone 50. Plate 3960 has a first hole 3962 and a second hole 3964 formed therein. A length between first hole 3962 and second hole 3964 is greater than a length between first surface 3920 and the second surface 3930 such that wedge 3900 is located between first hole 3962 and second hole 3964 so that bone fixation screws 3966 can be inserted through first hole 3962 and second hole 3964, and into bone 50 to secure plate 3962 bone 50 on either side of wedge 3900.

Optionally, plate 3960 can include a third hole 3968 disposed between first whole 3962 and second hole 3964, such that, when plate 3960 is affixed to bone 50 over wedge 3900, third hole 3968 is aligned with aperture 3940. A fixation screw 3970 is insertable through third hole 3968 and into aperture 3940 such that fixation screw 3970 secures fixation plate 3960 to wedge 3900.

An exemplary method of inserting wedge 3900 to stabilize and reposition a bone will now be discussed. First, a cut is made in bone 50 at an osteotomy site. Typically, the cut is only a partial cut, such that a portion of bone 50 on either side of the cut remains connected. Next, a forked wedge tool (not shown) is inserted into the cut and is used to open the osteotomy site. With an insertion instrument 1000 connected to wedge 3900 at aperture 3940, wedge 3900 is inserted into the cut. When wedge 3900 is properly positioned, insertion instrument 1000 is removed from wedge 3900, leaving wedge 3900 in the osteotomy site. Fixation plate 3960 is applied over wedge 3900 and secured to bone 50 on either side of wedge 3900 by fixation screws 3966.

Optionally, if third hole 3968 is present, fixation screw 3970 can be inserted through third hole 3968, and into aperture 3940, securing fixation plate 3960 directly to wedge 3900.

Optionally, each device described above that is to be implanted (i.e., interbody, wedge, screws, plate, etc.) can be coated with an antimicrobial agent, such as, for example, silver oxide. The anti-microbial coating can be in the form of a nano coating or other type of coating. Such an antimicrobial coating can be used to reduce or eliminate infections within the patient.

It should also be understood that this invention is not limited to the disclosed features and other similar method and system may be utilized without departing from the spirit and the scope of the invention.

While the invention has been described with reference to the preferred embodiment and alternative embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the claims. Further, it will be apparent to those of skill in the art that numerous changes may be made in such details without departing from the spirit and the principles of the invention. It should be appreciated that the invention is capable of being embodied in other forms without departing from its essential characteristics.

What is claimed is:

1. An osteotomy implant comprising:
   a first bone-engaging surface having a first plurality of longitudinal grooves and a second plurality of transverse grooves extending therealong such that portions of the first bone-engaging surface extend between adjacent longitudinal grooves and transverse grooves to form a first set of individual peaks;
   a second bone-engaging surface having a first plurality of longitudinal grooves and a second plurality of transverse grooves extending therealong such that portions of the second bone-engaging surface extend between adjacent longitudinal grooves and transverse grooves to form a second set of individual peaks; and
   a side surface extending between the first bone engaging surface and the second bone engaging surface,
   wherein each of the first set of individual peaks and the second set of individual peaks includes an osteoconductive coating and
   wherein the side surface is free from the osteoconductive coating,
   wherein the first bone-engaging surface and the second bone-engaging surface form a tapered wedge shape, wherein a first end of the first bone-engaging surface is disposed a first distance from a first end of the second bone-engaging surface, forming a first side wall having a first height, and wherein a second end of the first bone-engaging surface is disposed a second distance from a second end of the second bone-engaging surface, less than the first distance, forming a second side wall having a second height, less than the first height, and
   wherein the individual peaks in the first and second sets of individual peaks are tapered such that each of the individual peaks slopes toward the first side wall.

2. The osteotomy implant according to claim 1, further comprising a core disposed between the first bone-engaging surface and the second bone-engaging surface, the core being constructed from a radiolucent material.

3. The osteotomy implant according to claim 1, wherein the osteoconductive coating has a thickness of less than 800 microns.

4. The osteotomy implant according to claim 1, wherein the osteoconductive coating has a thickness of between 5 microns and 800 microns.

5. The osteotomy implant according to claim 1, wherein the osteoconductive coating is sufficiently thin such that the first bone-engaging surface and the second bone-engaging surface are transparent to imaging.

6. The osteotomy implant according to claim 1, wherein the osteoconductive coating is sufficiently thick such that the first bone-engaging surface and the second bone-engaging surface are visible to imaging.

7. The osteotomy implant according to claim 1, wherein the osteoconductive coating comprises a titanium plasma spray.

8. An osteotomy wedge system comprising:
   a. the osteotomy implant according to claim 1;
   b. a fixation plate having first and second holes formed therein, a length between the first and second holes being greater than a length between the first bone-engaging surface and the second bone-engaging surface of the implant; and
   c. a plurality of bone fixation screws adapted to secure the fixation plate to bone on either side of the implant.

9. The osteotomy wedge system according to claim 8, wherein a core of the implant has a threaded opening extending between the first bone-engaging surface and the second bone-engaging surface and wherein the fixation plate has a third hole between the first hole and the second hole such that, when the fixation plate is secured to bone, the third hole is axially aligned with the threaded opening.

10. The osteotomy wedge system according to claim 9, further comprising an insertion instrument releasably couplable to the threaded opening, the insertion instrument being releasably insertable through the third hole.

11. The osteotomy wedge system according to claim 10, further comprising a fixation screw sized to be insertable through the third hole and into the threaded opening such that the fixation screw secures the fixation plate to the osteotomy implant.

12. An osteotomy implant system comprising:
   a tapered wedge shaped core constructed from a radiolucent material, the core having a central plane extending therethrough;
   a first bone-engaging surface extending at a first acute angle relative to the central plane on a first side of the core, the first bone-engaging surface having a first side facing portion having a first plurality of individual peaks formed therein;
   a second bone-engaging surface disposed on an opposing, second side of the core, the second bone-engaging surface having a second side facing portion having a second plurality of individual peaks formed therein, the second bone-engaging surface extending at a second acute angle relative to the central plane such that the first and second bone-engaging surfaces form a tapered shape; and
   a side surface extending along the core between the first bone-engaging surface and the second bone-engaging surface, the side surface comprising a lateral portion having an opening formed therein such that the opening is configured to engage an insertion tool, a medial portion disposed distal from the lateral portion, an anterior portion extending between the lateral portion and the medial portion, and a posterior portion disposed distal from the anterior portion,
   wherein each of the first and second side facing portions along the anterior and posterior portions includes an osteoconductive coating,
   wherein the side surface between the first and second bone-facing surfaces is free from the osteoconductive coating, and
   wherein the first and second pluralities of individual peaks are tapered such that each of the individual peaks slopes toward the lateral portion.

13. The osteotomy implant system according to claim 12, wherein the core has a Young's modulus of between 0.5 GPa and 18 GPa.

14. The osteotomy implant system according to claim 12, wherein the osteoconductive coating is sufficiently thin to be undetected by imaging.

15. The osteotomy implant system according to claim 12, further comprising a fixation plate having a first opening and a second opening spaced from the first opening farther than a distance between the first bone engaging surface and the second bone engaging surface.

16. The osteotomy implant system according to claim 15, wherein the core comprises a peripheral portion having a threaded aperture formed therein.

17. The osteotomy implant system according to claim 16, wherein the fixation plate further has a third opening located between the first opening and the second opening such that, when the fixation plate is secured over the core, the third opening is aligned with the threaded aperture.

18. A method of inserting an osteotomy implant to stabilize and reposition a bone, the method comprising the steps of:
   a. making a cut in only a single bone at an osteotomy site; and
   b. inserting the osteotomy implant according to claim 1 into the cut.

19. The method according to claim 18, further comprising the step of, after step b., applying a fixation plate over the implant and securing the fixation plate to bone on either side of the implant.

20. The method according to claim 19, further comprising the step of inserting a fixation screw through the fixation plate and into the implant.

21. The method according to claim 19, further comprising the step of, between step a. and step b., inserting a wedge tool into the cut.

22. The method according to claim 19, wherein the step of making the cut comprises a partial osteotomy.

23. An implant for metatarsal/cuneiform arthrodesis, the implant comprising:
   a first bone-engaging surface having a first plurality of longitudinal grooves and a second plurality of transverse grooves extending therealong such that portions of the first bone-engaging surface extend between adjacent longitudinal grooves and transverse grooves to form a first set of individual peaks;
   a second bone-engaging surface having a first plurality of longitudinal grooves and a second plurality of transverse grooves extending therealong such that portions of the second bone-engaging surface extend between adjacent longitudinal grooves and transverse grooves to form a second set of individual peaks; and
   a side surface extending between the first bone-engaging surface and the second bone-engaging surface, the side surface comprising a lateral side wall having an aperture formed therein,
   wherein each of the first set of individual peaks and the second set of individual peaks includes an osteoconductive coating,
   wherein the side surface is free from the osteoconductive coating, and
   wherein the individual peaks in the first and second sets of individual peaks are tapered such that each of the individual peaks slopes toward the first side wall.

* * * * *